US012275932B2

(12) United States Patent
Lin et al.

(10) Patent No.: US 12,275,932 B2
(45) Date of Patent: Apr. 15, 2025

(54) TFT-BASED CELL ISOLATION DEVICE AND CELL MANIPULATION PANEL THEREOF

(71) Applicant: a.u. Vista, Inc., Irvine, CA (US)

(72) Inventors: Tung-Tsun Lin, Irvine, CA (US); Chih-Che Kuo, Hsinchu (TW); Yuan Mao, Irvine, CA (US)

(73) Assignee: A.U. VISTA, INC., Irvine, CA (US)

( * ) Notice: Subject to any disclaimer, the term of this patent is extended or adjusted under 35 U.S.C. 154(b) by 929 days.

(21) Appl. No.: 17/242,749

(22) Filed: Apr. 28, 2021

(65) Prior Publication Data

US 2022/0348863 A1 Nov. 3, 2022

(51) Int. Cl.
| | |
|---|---|
| *C12M 1/00* | (2006.01) |
| *C12M 1/36* | (2006.01) |
| *G01N 27/414* | (2006.01) |
| *G06V 20/69* | (2022.01) |

(52) U.S. Cl.
CPC ............ *C12M 47/04* (2013.01); *C12M 41/48* (2013.01); *G01N 27/4145* (2013.01); *G06V 20/693* (2022.01)

(58) Field of Classification Search
CPC ...... C12M 47/04; C12M 41/48; C12M 35/02; C12M 41/00; G01N 27/4145; G01N 27/414; G06V 20/693; C12N 13/00; G06T 7/0004; G06T 7/62; G06T 2207/10004; G06T 2207/30148
USPC ........................................................ 422/502
See application file for complete search history.

(56) References Cited

U.S. PATENT DOCUMENTS

| | | | |
|---|---|---|---|
| 8,547,111 B2 | 10/2013 | Hadwen et al. | |
| 2012/0007608 A1* | 1/2012 | Hadwen ................. | G09G 3/348 |
| | | | 324/649 |

FOREIGN PATENT DOCUMENTS

| | | |
|---|---|---|
| CN | 109174219 A | 1/2019 |
| CN | 109954526 A | 7/2019 |
| TW | 201736819 A | 10/2017 |
| TW | I680295 B | 12/2019 |
| WO | WO-2016104517 A1 * | 6/2016 ............... A01N 1/02 |
| WO | WO-2019122092 A1 * | 6/2019 ........ B01L 3/502707 |

* cited by examiner

*Primary Examiner* — Jill A Warden
*Assistant Examiner* — Jacqueline Brazin
(74) *Attorney, Agent, or Firm* — Tim Tingkang Xia, Esq.; Troutman Pepper Locke LLP

(57) ABSTRACT

A cell manipulation panel includes a pixel array defining multiple pixels, an insulating layer forming multiple vias, and a cell gap provided with a fluid medium having cells therein. Each pixel has a TFT and corresponds to a corresponding via. The TFT includes a gate electrode, a first electrode, and a second electrode partially exposed to the fluid medium through the corresponding via. For each pixel, in an operational mode, when the gate electrode is provided with an OFF signal and the first electrode is not grounded, the TFT is turned off, allowing one of the cells in the fluid medium to be captured in the corresponding via by a dielectrophoresis (DEP) force. When the gate electrode is provided with an ON signal and the first electrode is grounded, the TFT is turned on, and the second electrode is grounded to release the captured cell to the fluid medium.

7 Claims, 29 Drawing Sheets

TFT-BASED CELL ISOLATION DEVICE AND CELL MANIPULATION PANEL THEREOF

FIELD

The disclosure relates generally to cell isolation and manipulation technology, and more particularly to a thin-film transistor (TFT)-based cell isolation device and a cell manipulation panel thereof.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

In order to better understand the function and variation of cells, researchers need to study a single cell to develop better drug formulation to prevent infectious diseases. Cell isolation and manipulation is essential for further analysis and will be valuable for diagnostics, biotechnological and biomedical applications in precision medicine.

Currently, there are multiple methods that can be used for cell isolation and manipulation. For example, one of the methods is an Optically Induced Dielectrophoresis (ODEP) Microfluidic System. Specifically, the ODEP Microfluidic system is provided with a phtoconductive layer with virtual electrodes. When projected light illuminates the photoconductive layer, it turns on the virtual electrodes, creating non-uniform electric fields and enabling particle manipulation via DEP forces. High resolution and collimated light source to create virtual electrodes is critical for achieving ODEP cell manipulation.

However, the conventional ODEP cell manipulation device requires a light source to generate an electric field and the resulting ODEP force, which consumes more power. Further, the light source requires small field-of-view (FOV) to maintain the optical resolution for conventional ODEP cell manipulation device, because a blurry light beam may cause a significant decrease in DEP forces. Moreover, the conventional cell manipulation device cannot achieve cell manipulation over a large area.

Therefore, a heretofore unaddressed need exists in the art to address the aforementioned deficiencies and inadequacies.

SUMMARY

One aspect of the disclosure relates to a cell manipulation panel, which includes: a first substrate and a second substrate spaced apart, forming a cell gap therebetween, wherein the cell gap is configured to be provided with a fluid medium having a plurality of cells therein; an insulating layer disposed on the first substrate, forming a plurality of vias penetrating therethrough; a pixel array disposed between the insulating layer and the first substrate, defining a plurality of pixels, wherein each of the pixels has a first thin film transistor (TFT) and corresponds to a corresponding via of the vias, the first TFT comprises a first gate electrode, a first electrode and a second electrode, the first gate electrode is provided with a first gate signal, the first gate signal is switched between an ON signal and an OFF signal, the first electrode is configured to be grounded, and the second electrode is located corresponding to the corresponding via such that the second electrode is partially exposed to the fluid medium in the cell gap through the corresponding via; a common electrode disposed on the second substrate, being provided with a common voltage $V_{COM}$; and a plurality of bottom electrodes disposed between the insulating layer and the first substrate, wherein each of the bottom electrodes is configured to be provided with a bottom voltage in an operational mode. For each of the pixels, in the operational mode, when the first gate signal is the OFF signal and the first electrode is not grounded, the first TFT is turned off, and one of the cells is captured in the corresponding via from the fluid medium by a dielectrophoresis (DEP) force; and when the first gate signal is the ON signal and the first electrode is grounded, the first TFT is turned on, and the second electrode is grounded to release the one of the cells being captured to the fluid medium.

In certain embodiments, the bottom voltage is an inverse signal of the common voltage to increase the DEP force.

In certain embodiments, the cells comprises wanted cells and unwanted cells, and the unwanted cells are lightened.

In certain embodiments, the unwanted cells are lightened by a reagent.

In certain embodiments, each of the vias has a diameter of 5 um, a pitch between two adjacent ones of the vias is in a range of 20-50 um, and each of the cells has a cell diameter of 5 um.

In certain embodiments, the cell manipulation panel further includes: a plurality of first gate lines, correspondingly connected to the first gate electrodes of the pixels, wherein each of the first gate lines is configured to provide the first gate signal to the first gate electrode of a corresponding one of the pixels; a plurality of grounding lines, correspondingly connected to the first electrodes of the pixels; a plurality of second TFTs, one-to-one correspondingly connected to the grounding lines, wherein each of the second TFTs comprises a second gate electrode, a third electrode and a fourth electrode, the second gate electrode is provided with a second gate signal, the second gate signal is switched between an ON signal and an OFF signal, the third electrode is grounded, and the fourth electrode is electrically connected to a corresponding one of the grounding lines; and a plurality of second gate lines, correspondingly connected to the second gate electrodes of the second TFTs, wherein each of the second gate lines is configured to provide a second gate signal to the second gate electrodes of the of a corresponding one of the second TFTs. wherein for each of the pixels, in the operational mode, when the first gate signal is the OFF signal and the first electrode is not grounded, the first TFT is turned off, and one of the cells is captured in the corresponding via from the fluid medium by a dielectrophoresis (DEP) force; and when the first gate signal is the ON signal and the first electrode is grounded, the first TFT is turned on, and the second electrode is grounded to release the one of the cells being captured to the fluid medium.

In certain embodiments, the second substrate has an inlet and an outlet in communication with the cell gap.

In another aspect of the disclosure, a cell isolation device is provided, which includes the cell manipulation panel as described above, wherein the cells comprises wanted cells and unwanted cells, and the unwanted cells are lightened; an imaging device, disposed on a side of the cell manipulation panel adjacent to one of the first substrate and the second substrate, configured to capture an image of the pixels having cells being captured in the vias; and a controller, communicatively connected to the imaging device and the cell manipulation panel, wherein the controller is configured to:control a first gate driver to provide either the ON signal or the OFF signal as the first gate signal to each of the pixels; control a second gate driver to provide a second gate signal to control the first electrode of each of the pixels to be grounded or not to be grounded; control the cell manipulation panel to capture the cells in the pixels; receive the image obtained by the imaging device; analyze the image and determine the pixels having the wanted cells being captured therein and the pixels having the unwanted cells being captured therein; and in response to determining the pixels having the unwanted cells being captured therein, control the cell manipulation panel to release the unwanted cells to the fluid medium.

In certain embodiments, the cell manipulation panel further comprises: a plurality of first gate lines, correspondingly connected to the first gate driver and the first gate electrodes of the pixels, wherein each of the first gate lines is configured to provide the first gate signal to the first gate electrode of a corresponding one of the pixels; a plurality of grounding lines, correspondingly connected to the first electrodes of the pixels; a plurality of second TFTs, one-to-one correspondingly connected to the grounding lines, wherein each of the second TFTs comprises a second gate electrode, a third electrode and a fourth electrode, the second gate electrode is provided with a second gate signal, the second gate signal is switched between an ON signal and an OFF signal, the third electrode is grounded, and the fourth electrode is electrically connected to a corresponding one of the grounding lines; and a plurality of second gate lines, correspondingly connected to a second gate driver and the second gate electrodes of the second TFTs, wherein each of the second gate lines is configured to provide a second gate signal to the second gate electrodes of the of a corresponding one of the second TFTs.

In certain embodiments, the controller is configured to the cell manipulation panel to capture the cells in the pixels by: controlling the first gate driver to provide the OFF signal as the first gate signals to all of the pixels through the first gate lines; and controlling the second gate driver to provide the OFF signal as the second gate signals to the second gate electrodes of all of the second TFTs through the second gate lines.

In certain embodiments, the controller is configured to control the cell manipulation panel to release the unwanted cells to the fluid medium by: determining a specific pixel of the pixels to have one of the unwanted cells being captured therein; controlling the first gate driver to provide the ON signal as the first gate signal to the specific pixel through a corresponding one of the first gate lines; and controlling the second gate driver to provide the ON signal as the second gate signal to the second gate electrode of a corresponding one of the second TFTs through the second gate lines, such that the corresponding one of the second TFTs is turned on, and the first electrode of the specific pixel is grounded through a corresponding one of the grounding lines being connected to the corresponding one of the second TFTs.

In certain embodiments, the controller is configured to control the cell manipulation panel to release the unwanted cells to the fluid medium by: determining a specific pixel of the pixels to have one of the unwanted cells being captured therein; controlling the second gate driver to sequentially provide the ON signal as the second gate signal to the second gate electrode of each of the second TFTs through the second gate lines; and when a corresponding one of the second TFTs is turned on, such that the first electrode of the specific pixel is grounded through a corresponding one of the grounding lines being connected to the corresponding one of the second TFTs, controlling the first gate driver to provide the ON signal as the first gate signal to the specific pixel through a corresponding one of the first gate lines.

In certain embodiments, the bottom voltage is an inverse signal of the common voltage to increase the DEP force.

In yet another aspect of the disclosure, a method of performing cell manipulation includes: providing the cell manipulation panel as discussed above, wherein the cells comprises wanted cells and unwanted cells, and the unwanted cells are lightened; providing the fluid medium into the cell gap; controlling, by a controller, the cell manipulation panel to capture the cells in the pixels; obtaining, by an imaging device, the image of the pixels having the cells being captured in the vias; analyzing, by the controller, the image and determining the pixels having the wanted cells being captured therein and the pixels having the unwanted cells being captured therein; in response to determining the pixels having the unwanted cells being captured therein, controlling, by the controller, the cell manipulation panel to release the unwanted cells to the fluid medium; and in response to releasing the unwanted cells, pumping out the fluid medium from the cell gap.

In certain embodiments, the method further includes: adding a reagent in the fluid medium to lighten the unwanted cells.

In certain embodiments, the cell manipulation panel further comprises: a plurality of first gate lines, correspondingly connected to a first gate driver and the first gate electrodes of the pixels, wherein each of the first gate lines is configured to provide the first gate signal to the first gate electrode of a corresponding one of the pixels; a plurality of grounding lines, correspondingly connected to the first electrodes of the pixels; a plurality of second TFTs, one-to-one correspondingly connected to the grounding lines, wherein each of the second TFTs comprises a second gate electrode, a third electrode and a fourth electrode, the second gate electrode is provided with a second gate signal, the second gate signal is switched between an ON signal and an OFF signal, the third electrode is grounded, and the fourth electrode is electrically connected to a corresponding one of the grounding lines; and a plurality of second gate lines, correspondingly connected to a second gate driver and the second gate electrodes of the second TFTs, wherein each of the second gate lines is configured to provide a second gate signal to the second gate electrodes of the of a corresponding one of the second TFTs.

In certain embodiments, the controller is configured to the cell manipulation panel to capture the cells in the pixels by: controlling the first gate driver to provide the OFF signal as the first gate signals to all of the pixels through the first gate lines; and controlling the second gate driver to provide the OFF signal as the second gate signals to the second gate electrodes of all of the second TFTs through the second gate lines.

In certain embodiments, the controller is configured to control the cell manipulation panel to release the unwanted cells to the fluid medium by: determining a specific pixel of the pixels to have one of the unwanted cells being captured therein; controlling the first gate driver to provide the ON signal as the first gate signal to the specific pixel through a corresponding one of the first gate lines; and controlling the second gate driver to provide the ON signal as the second gate signal to the second gate electrode of a corresponding one of the second TFTs through the second gate lines, such that the corresponding one of the second TFTs is turned on, and the first electrode of the specific pixel is grounded through a corresponding one of the grounding lines being connected to the corresponding one of the second TFTs.

In certain embodiments, the controller is configured to control the cell manipulation panel to release the unwanted cells to the fluid medium by: determining a specific pixel of the pixels to have one of the unwanted cells being captured therein; controlling the second gate driver to sequentially provide the ON signal as the second gate signal to the second gate electrode of each of the second TFTs through the second gate lines; and when a corresponding one of the second TFTs is turned on, such that the first electrode of the specific pixel is grounded through a corresponding one of the grounding lines being connected to the corresponding one of the second TFTs, controlling the first gate driver to provide the ON signal as the first gate signal to the specific pixel through a corresponding one of the first gate lines.

In certain embodiments, the method further includes: collecting the fluid medium being pumped out of the cell gap, wherein the fluid medium being pumped out includes the unwanted cells being filtered.

These and other aspects of the present invention will become apparent from the following description of the preferred embodiment taken in conjunction with the following drawings, although variations and modifications therein may be effected without departing from the spirit and scope of the novel concepts of the disclosure.

BRIEF DESCRIPTION OF THE DRAWINGS

The accompanying drawings illustrate one or more embodiments of the disclosure and together with the written description, serve to explain the principles of the disclosure. Wherever possible, the same reference numbers are used throughout the drawings to refer to the same or like elements of an embodiment, and wherein.

DETAILED DESCRIPTION OF THE DISCLOSURE

Figure 1B:
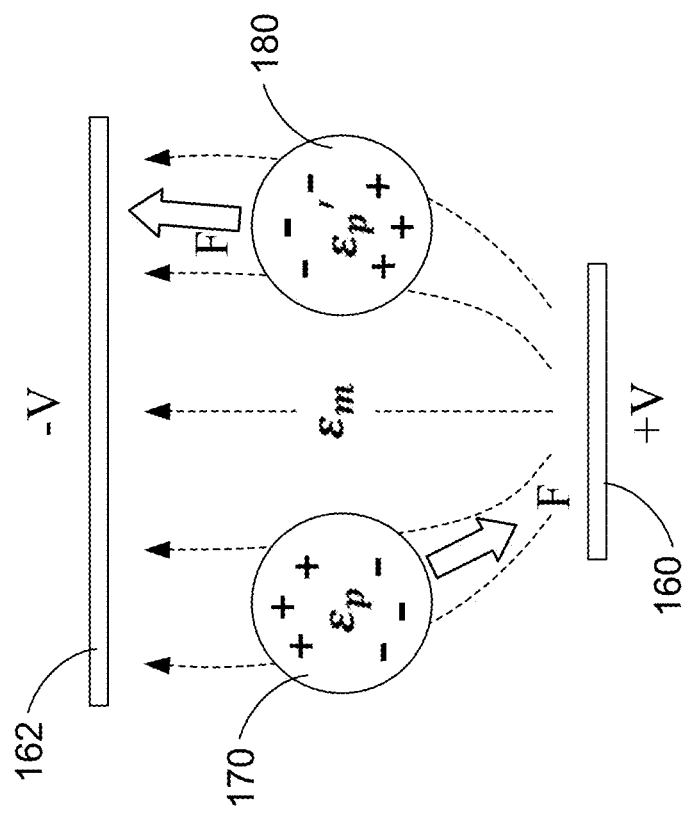
FIG. 1B schematically shows the DEP forces acted on particles in a non-uniform electric field according to certain embodiments of the present disclosure.

The present disclosure will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", or "includes" and/or "including" or "has" and/or "having" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom", "upper" or "top", and "left" and "right", may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper", depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The description will be made as to the embodiments of the present disclosure in conjunction with the accompanying drawings. In accordance with the purposes of this disclosure, as embodied and broadly described herein, this disclosure, in certain aspects, relates to a blended display device.

As discussed, in a conventional Microfluidic system, when the projected light illuminates the photoconductive layer, it turns on the virtual electrodes, creating non-uniform electric fields and enabling particle manipulation via DEP forces. Specifically, for particles in a fluid, the forces acted on the particles may be summarized in the following equations (1)-(4), where the equation (1) is a sum of three separate terms of forces as shown in equations (2)-(4):

$$F = F1 + F2 + F3 \tag{1}$$

$$F1 = \frac{1}{\tau_p} m_p (u - v) \tag{2}$$

$$F2 = \zeta \sqrt{\frac{12\pi k_B \mu T r_p}{\Delta t}} \tag{3}$$

$$F3 = 2\pi r_p^3 \varepsilon_0 \varepsilon_r \kappa \nabla |E|^2 \tag{4}$$

In particular, the first term F1 is the drag force, which is proportional to the relative velocity (u-v) between the particles and the fluid, and is relatively large and dominated by fluid velocity. The second term F2 is the Brownian force, which depends on the temperature T of the fluid and the radius r of the particles, and is relatively small and dominated by the temperature. The third term F3 is the DEP force, which is proportional to the gradient of the electric field, and is relatively large and dominated by the electric field applied.

Figure 1A:
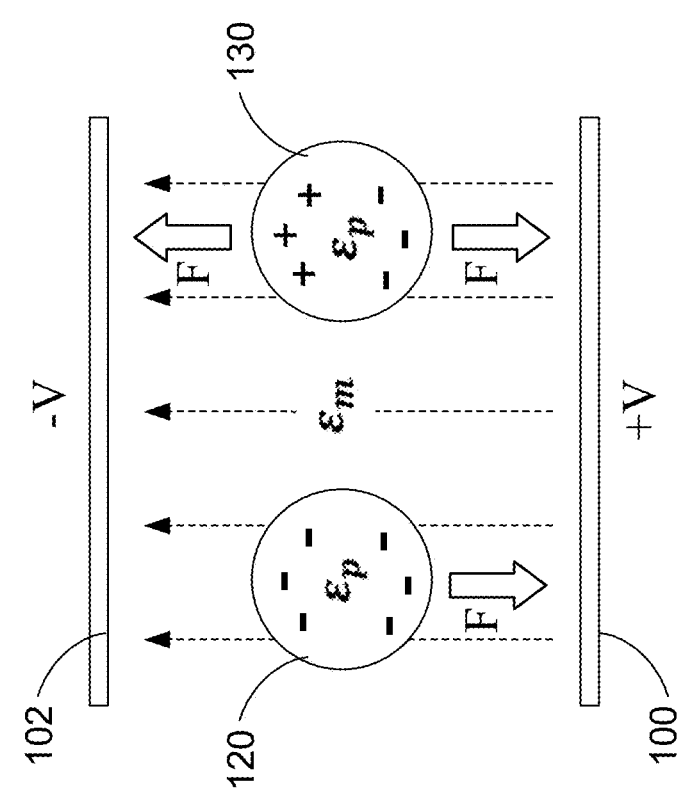
FIG. 1A schematically shows the forces acted on particles in a uniform electric field according to certain embodiments of the present disclosure.

FIG. 1A schematically shows the forces acted on particles in a uniform electric field according to certain embodiments of the present disclosure, and FIG. 1B schematically shows the DEP forces acted on particles in a non-uniform electric field according to certain embodiments of the present disclosure. Specifically, as shown in FIG. 1A, two electrodes 100 and 102 are provided with substantially the same size, where the electrode 100 provides a positive voltage +V, and the electrode 102 provides a negative voltage −V, forming a uniform electric field. Further, a fluid medium having a permittivity $\varepsilon_m$ is provided between the two electrodes 100 and 102, and two exemplary particles 120 and 130 are provided in the fluid medium. Each of the two particles 120 and 130 has a permittivity $\varepsilon_p$. The two particles 120 and 130 include a charged particle 120, which is negatively charged, and a neutral particle 130. In this case, the charged particle 120, which is negatively charged, is subject to a force F toward the electrode 100, and the neutral particle 130 is subject to two opposite and equally balanced forces F, regardless of the value of the permittivities $\varepsilon_m$ and $\varepsilon_p$. In comparison, as shown in FIG. 1B, two electrodes 160 and 162 are provided with substantially different size, where the smaller electrode 160 provides a positive voltage +V, and the larger electrode 162 provides a negative voltage −V, forming a non-uniform electric field. Further, a fluid medium having a permittivity $\varepsilon_m$ is provided between the two electrodes 160 and 162, and two exemplary neutral particles 170 and 180 are provided in the fluid medium. The neutral particle 170 has a permittivity $\varepsilon_p$, and the neutral particle 170 has a permittivity $\varepsilon_p'$, where $\varepsilon_p'>\varepsilon_m$ and $\varepsilon_p'<\varepsilon_m$. In this case, the neutral particle 170, which has a larger permittivity than that of the fluid medium, is subject to a force F toward the electrode 160, and the neutral particle 180, which has a smaller permittivity than that of the fluid medium, is subject to a force F toward the electrode 120. An example of the neutral particle 180 having a smaller permittivity than that of its surrounding fluid medium is the red blood cell in the blood.

More specifically, for a particle, the DEP force $F_{dep}$ may be shown in the following equations (5)-(7):

$$F_{dep} = 2\pi r_p^3 \varepsilon_0 \text{ real } (\varepsilon_r^*) \text{ real} \left( \frac{\varepsilon_{r,p}^* - \varepsilon_r^*}{\varepsilon_{r,p}^* + 2\varepsilon_r^*} \right) \nabla |E_{rms}|^2 \quad (5)$$

$$\varepsilon^* = \varepsilon - \frac{i\sigma}{\omega} \quad (6)$$

$$\omega = 2\pi f \quad (7)$$

where $\varepsilon$ (SI unit: F/m) is the permittivity, $\sigma$ (SI unit: S/m) is the electrical conductivity, co (SI unit: Hz) is the angular frequency of the electric field, $r_p$ (SI unit: m) is the radius of a spherical particle in the electric field, $\varepsilon_0$ is the vacuum permittivity (where $\varepsilon_0=8.854187817*10^{-12}$ F/m), $\varepsilon_r^*$ (dimensionless) is the complex relative permittivity of the fluid medium, $\varepsilon_{r,p}^*$ (dimensionless) is the complex relative permittivity of the particle, and $E_{rms}$ (SI unit: V/m) is the root mean square electric field.

In certain embodiments, if the particles are provided with thin dielectric shells, the following equation (8) may apply:

$$\varepsilon_{eq}^* = \varepsilon_s^* \frac{\left(\frac{r_o}{r_i}\right)^3 + 2\left(\frac{\varepsilon_{r,p}^* - \varepsilon_{r,s}^*}{\varepsilon_{r,p}^* + 2\varepsilon_{r,s}^*}\right)}{\left(\frac{r_o}{r_i}\right)^3 - \left(\frac{\varepsilon_{r,p}^* - \varepsilon_{r,s}^*}{\varepsilon_{r,p}^* + 2\varepsilon_{r,s}^*}\right)} \quad (8)$$

where $r_o$ and $r_i$ (SI unit: m) are the outer and inner radii of the shell, respectively, $\varepsilon_{r,p}^*$ (dimensionless) is the complex relative permittivity of the particle, and $\varepsilon_{r,s}^*$ (dimensionless) is the complex relative permittivity of the outer shell.

Figure 2:
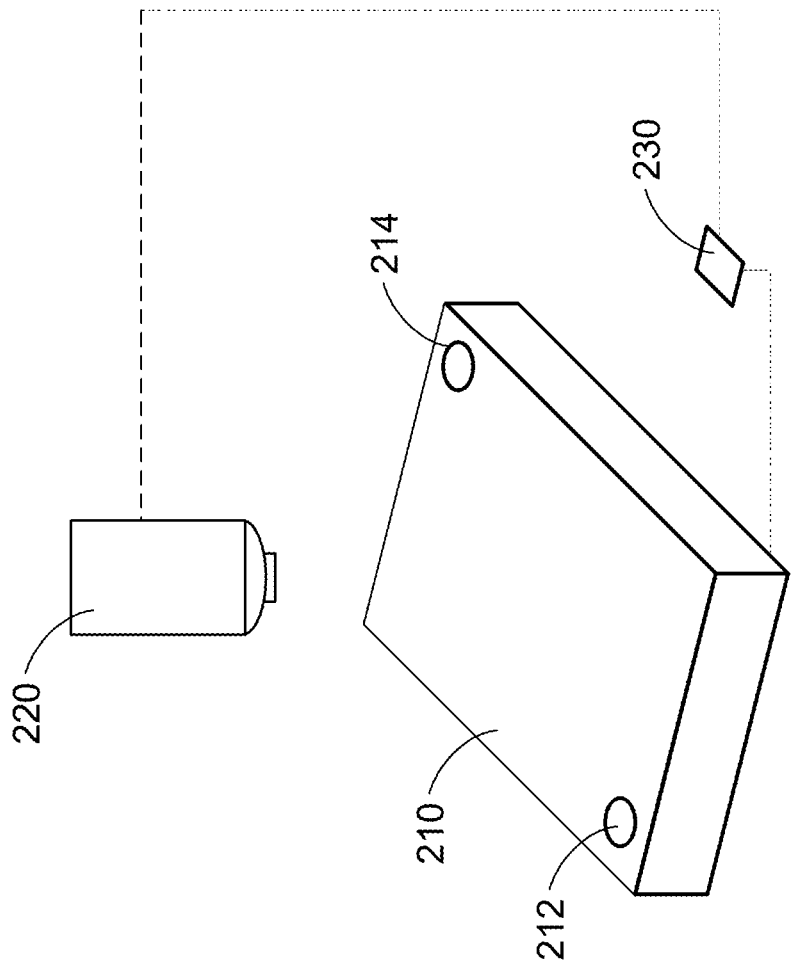
FIG. 2 schematically shows a cell isolation device according to certain embodiments of the present disclosure.

FIG. 2 schematically shows a cell isolation device according to certain embodiments of the present disclosure. Specifically, the cell isolation device 200 as shown in FIG. 2 may be used to perform cell isolation, manipulation, filtering, purification, or other similar operation to the cells. As shown in FIG. 2, the cell isolation device 200 includes a cell manipulation panel 210, an imaging device 220 and a controller 230. The cell manipulation panel 210 is a panel shaped device, which is formed by two transparent substrates having a cell gap therebetween, and a pixel array defining a plurality of pixels, where the cell gap is used as a passage of a fluid medium having a plurality of cells therein, and each pixel may be used to capture or release the cells. As shown in FIG. 2, the cell manipulation panel 210 has an inlet 212 and an outlet 214 disposed on the top substrate, where the inlet 212 and the outlet 214 are respectively in communication with the cell gap, allowing the fluid medium to flow through the inlet 212, the cell gap and the outlet 214. The imaging device 220 is disposed on a top side of the cell manipulation panel 210 and is adjacent to the top transparent substrate, and is capable of capturing an image of the pixels having cells being captured therein. In certain embodiments, the imaging device 220 may be a charged-coupled device (CCD), a camera or other imaging devices. In one embodiment, it is also possible to dispose the imaging device 220 on a bottom side of the cell manipulation panel 210 to be adjacent to the bottom transparent substrate. The controller 230 is communicatively connected to the imaging device 220 and the cell manipulation panel 210 to control the operation of the imaging device 220 and the cell manipulation panel 210. In certain embodiments, the controller 230 may be a system on a chip (SoC) or other computing device embedded on the cell manipulation panel 210. In one embodiment, the cell isolation device 200 may be in the form and size of a portable device or a mobile device, allowing a user to carry it.

Figure 3:
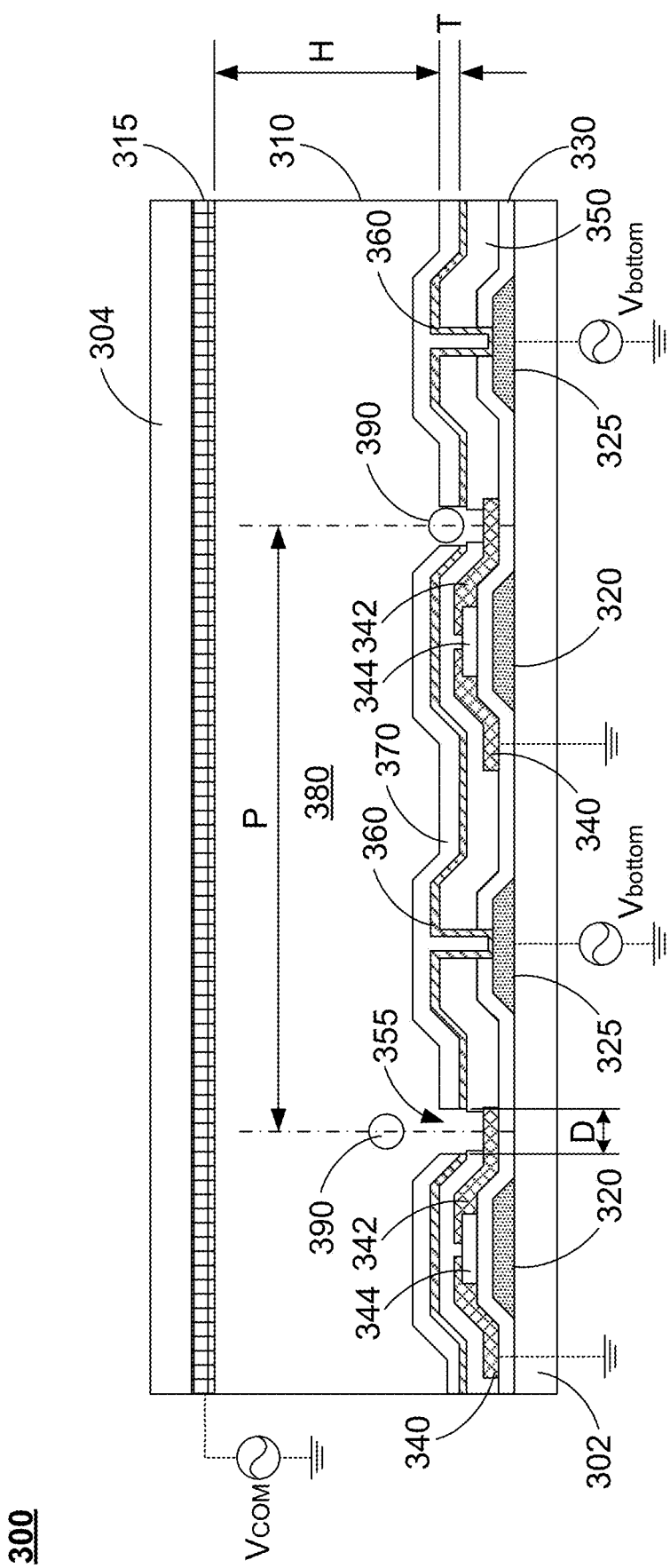
FIG. 3 schematically shows a partial cross-sectional view of a cell manipulation panel according to one embodiment of the present disclosure.

FIG. 3 schematically shows a partial cross-sectional view of a cell manipulation panel according to one embodiment of the present disclosure. Specifically, the cell manipulation panel 300 may be used as the cell manipulation panel 210 in the cell isolation device 200 as shown in FIG. 2. As shown in FIG. 3, the cell manipulation panel 300 includes a first substrate (i.e., the bottom substrate) 302 and a second substrate (i.e., the top substrate) 304 spaced apart, forming a cell gap 310 therebetween. The cell gap 310 is used as a passage for a fluid medium 380 having a plurality of cells 390 therein to pass therethrough. As shown in FIG. 3, the cell gap 310 has a height H. In one embodiment, the height of the cell gap 310 can be 60 um.

On the first substrate 302, there are multiple layers disposed thereon to form a pixel array to define a plurality of pixels. Specifically, FIG. 3 shows two adjacent pixels arranged in the left-right direction. Further, a common electrode 315 is disposed on the second substrate 304, and is provided with an alternate current (AC) voltage signal as a common voltage $V_{COM}$. In certain embodiments, the common voltage $V_{COM}$ may be an AC voltage signal between +10V and −10V with a frequency of 10 MHz. As shown in FIG. 3, for each of the pixels, the layers disposed on the first substrate 302 include a first gate electrode 320, a bottom electrode 325, a gate insulating layer 330 disposed on first substrate 302 covering the first gate electrode 320 and the bottom electrode 325, a first electrode (i.e., the source electrode) 340, a second electrode (i.e., the drain electrode) 342 and a semiconductor layer 344 disposed on the gate insulating layer 330, a first insulating layer 350 disposed to cover the first electrode 340 and the semiconductor layer 344 and to partially cover the second electrode 342, a metal layer 360 electrically connected to the bottom electrode 325, and a second insulating layer 370 disposed on the metal layer 360. Specifically, the first gate electrode 320, the first electrode 340, the second electrode 342 and the semiconductor layer 344 collectively form a first TFT for the pixel. The second insulating layer 370 has a thickness T. In one embodiment, the thickness T can be 0.5 um.

In addition, for each of the pixels, a via 355 is formed to penetrate through the first insulating layer 350, the metal layer 360 and the second insulating layer 370, such that a portion of the second electrode 342 is correspondingly exposed to the fluid medium 380 through the via 355. In this case, for each pixel, the first TFT one-to-one corresponds to the via 355. As shown in FIG. 3, in the pixel in the left side, there is no corresponding cell 390 being captured in the via 355, and in the pixel at the right side, a corresponding cell 390 is captured in the via 355. The diameter of the via 355 is D, which corresponds to the cell diameter of the cells 390 (such that a corresponding cell 390 may be captured in the via 355 without escaping from the DEP force), and there is a pitch distance P between the vias 355 of the two adjacent pixels. In certain embodiments, the pitch distance P between the two vias 355 may be in the range of 20-50 um. In one embodiment, the diameter D of the via 355 may be 5 um, and the pitch distance P between the two vias 355 may be 40 um. Thus, each of the cells 390 may also have a cell diameter of 5 um.

Further, as shown in FIG. 3, the first electrode 340 is configured to be grounded, and the bottom electrode 325 is provided with an AC voltage signal as a bottom voltage $V_{bottom}$. Since the bottom electrode 325 is electrically connected to the metal layer 360, the configuration of the common electrode 315, the metal layer 360 and the exposed portion of the second electrode 342 may provide a non-uniform electric field, which is similar to the case as shown in FIG. 1B, to generate the DEP force that may be used to capture the cells 390. In certain embodiments, to increase the DEP force generated by the non-uniform electric field, the bottom voltage $V_{bottom}$ may be an inverse signal of the common voltage $V_{COM}$. For example, when the common voltage $V_{COM}$ is an AC voltage signal between +10V and -10V with a frequency of 10 MHz, the bottom voltage $V_{bottom}$ may be an inverse AC voltage signal between -10V and +10V with the same frequency of 10 MHz. In certain embodiments, the bottom voltage $V_{bottom}$ may also be other signals. For example, the bottom electrode 325 may be grounded, and the bottom voltage $V_{bottom}$ is 0V.

Figure 4A:
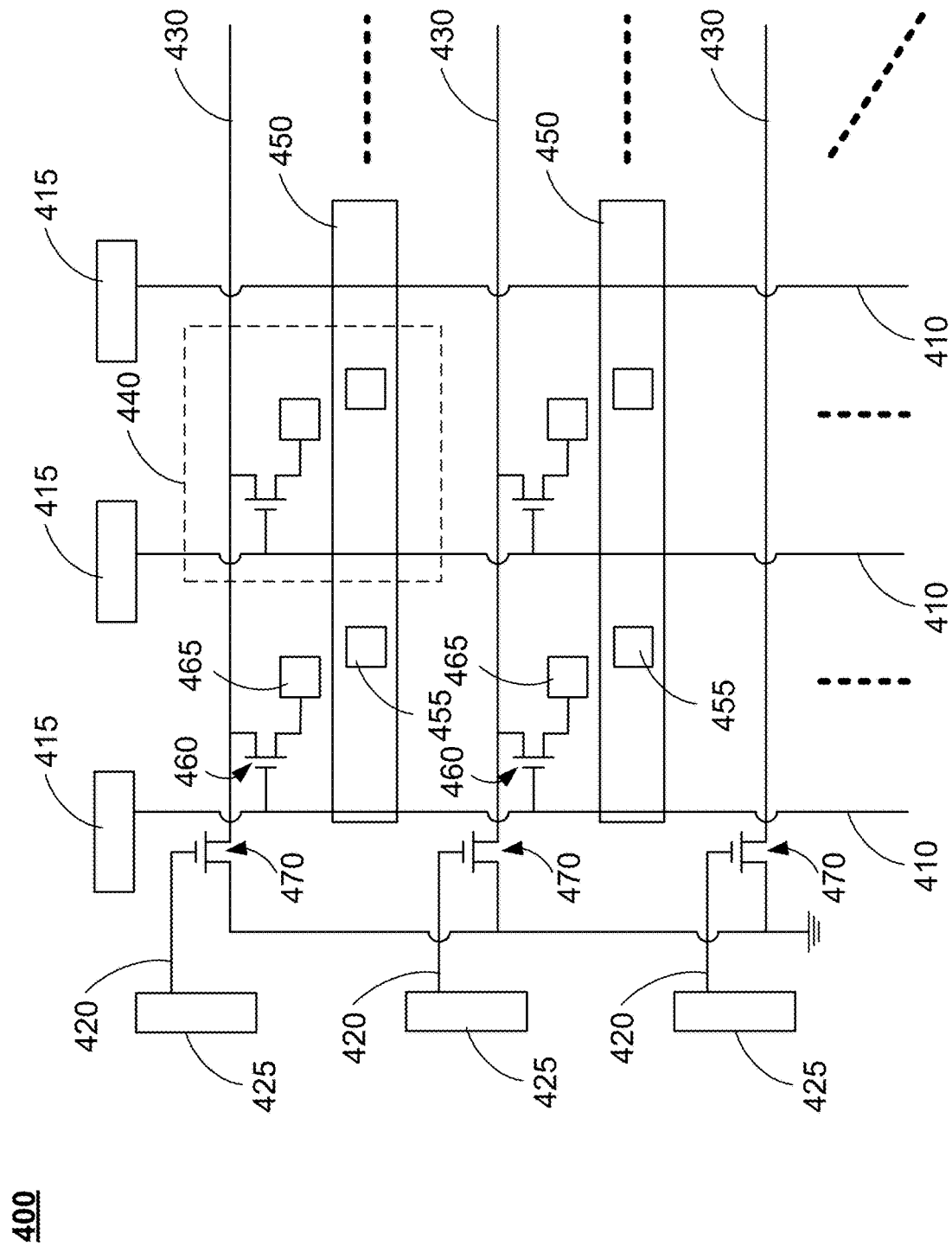
FIG. 4A schematically shows circuitry of a pixel array of the cell manipulation panel according to one embodiment of the present disclosure.
Figure 4B:
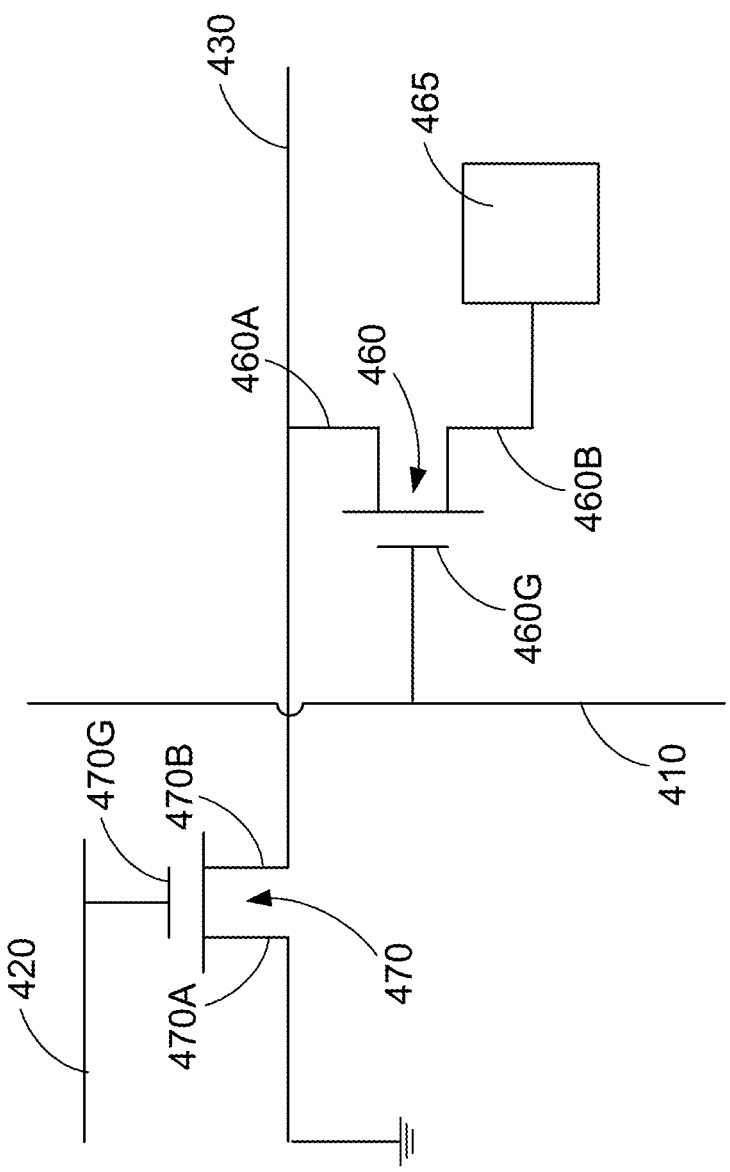
FIG. 4B schematically shows a partially enlarged pixel of FIG. 4A.

FIG. 4A schematically shows circuitry of a pixel array of the cell manipulation panel according to one embodiment of the present disclosure, and FIG. 4B schematically shows a partially enlarged pixel of FIG. 4A. As shown in FIG. 4A, the cell manipulation panel 400 includes a plurality of first gate lines 410 substantially extending along a first direction (i.e., the vertical direction as shown in FIG. 4A), a plurality of first gate drivers 415, a plurality of second gate lines 420 substantially extending along a second direction (i.e., the horizontal direction as shown in FIG. 4A) a plurality of second gate drivers 425, a plurality of grounding lines 430 substantially extending along the second direction (i.e., the horizontal direction as shown in FIG. 4A), a plurality of bottom connecting lines 450 extending along the second direction (i.e., the horizontal direction as shown in FIG. 4A), a plurality of second TFTs 470, and a plurality of pixels 440. The first gate drivers 415 and the second gate drivers 425 may be communicatively connected to the controller of the cell isolation device. Each pixel 440 includes a bottom electrode 455 (i.e., the bottom electrode 325 as shown in FIG. 3), a first TFT 460, and a via 465 (i.e., the via 355 as shown in FIG. 3). As shown in FIG. 4B, each first TFT 460 includes a first gate electrode 460G (i.e., the first gate electrode 320 as shown in FIG. 3), a first electrode 460A (i.e., the first electrode 340 as shown in FIG. 3), and a second electrode 460B (i.e., the second electrode 342 as shown in FIG. 3). Each second TFT 470 includes a second gate electrode 470G, a third electrode 470A, and a fourth electrode 470B.

The first gate lines 410 extend along the first direction to correspondingly connect the first gate drivers 415 to the first gate electrodes 460G of the first TFTs 470 of the pixels 440. Specifically, each first gate lines 410 corresponds to a column of the pixels 440. The first gate drivers 415 are used to be controlled by the controller of the cell isolation device to generate the first gate signals (each being switchable between an ON signal and an OFF signal) for the first gate electrodes 460G of the first TFTs 460 of the pixels, and the first gate lines 410 are used to provide the first gate signals generated by the first gate drivers 415 to the first gate electrodes 460G to control the first TFTs 460 to turn on or turn off. When the first TFT 460 of a specific pixel 440 is turned on, the first electrode 460A and the second electrode 460B of the first TFT 460 are electrically connected. In this case, if the first electrode 460A is grounded, the second electrode 460B is correspondingly grounded.

The second gate lines 420 extend along the second direction to correspondingly connect the second gate drivers 425 to the second gate electrodes 470G of the second TFTs 470. The grounding lines 430 extend along the second direction to correspondingly connect the fourth electrodes 470B of the second TFT 470 and the first electrodes 460A of the first TFTs 460 of the pixels 440. Specifically, each second gate line 420 one-to-one corresponds to a corresponding second TFT 470, and each grounding line 430 one-to-one corresponds to a corresponding second TFT 470 and a row of the pixels 440. The second gate drivers 425 are used to be controlled by the controller of the cell isolation device to generate the second gate signals (each being switchable between an ON signal and an OFF signal) for the second gate electrodes 470G of the second TFTs 470, and each second gate line 420 is used to provide the corresponding second gate signal generated by the second gate driver 425 to the second gate electrode 470G to control the corresponding second TFT 470 to turn on or turn off. When a specific second TFT 470 is turned on, the first electrodes of the first TFTs 460 of the corresponding row of the pixels 440 are all grounded. On the other hand, when the specific second TFT 470 is turned off, the first electrodes of the first TFTs 460 of the corresponding row of the pixels 440 are not grounded.

The bottom connecting lines 450 extend along the second direction to correspondingly connect the bottom electrodes 455 of a corresponding row of the pixels 440. In certain embodiments, the bottom connecting lines 450 may be electrically interconnected such that the bottom voltage $V_{bottom}$ provided to the bottom electrodes 455 of all pixels 440 are identical.

When the cell modulation panel 400 is in an operational mode, the operation for each pixel 440 is controlled by the corresponding first and second TFTs, which may be respectively turned on or off by the corresponding first and second gate signals. Specifically, for a specific pixel 440, when the corresponding first and second gate signals are both OFF signals, the first electrode 460A of the first TFT 460 of the specific pixel 440 is not grounded, and the first TFT is turned off. In this case, due to the non-uniform electric field generated by the second electrode 460B, the metal layer and the common electrode, a corresponding cell is captured in the corresponding via 465 from the fluid medium by the DEP force. On the other hand, when the corresponding first and second gate signals are both ON signals, the first electrode 460A of the first TFT 460 of the specific pixel 440 is grounded, and the first TFT 460 is turned on. In this case, the second electrode 460B of the first TFT 460 of the specific pixel 440 is also grounded, thus releasing the cell being captured in the via 465 to the fluid medium.

In certain embodiments, the cells in the fluid medium may include wanted cells and unwanted cells, such that the cells can be manipulated or isolated to obtain the wanted cells. For example, in one embodiment, the fluid medium may include normal cells and abnormal cells (e.g., cancerous cells), and one of the normal and abnormal cells may be wanted, while the other is unwanted. In certain embodiments, the determination of the wanted and unwanted cells may be based on the need or purpose of cell manipulation or isolation. For example, when the purpose of cell manipulation or isolation is to filter one specific type of the cells from all the cells for further analysis, the specific type of the cells may be the wanted cells. In one embodiment, to perform cell manipulation or isolation, the unwanted cells can be lightened. For example, the unwanted cells may be lightened by a reagent, such as a specific enzyme.

Referring back to FIG. 2, in the cell isolation device 200, the controller 230 may be used to control each of the first gate drivers 415 to provide either the ON signal or the OFF signal as the first gate signal to each of the pixels; control each of the second gate drivers 425 to provide a second gate signal to control the first electrode of each of the pixels to be grounded or not to be grounded; control the cell manipulation panel 210 to capture the cells in the pixels; receive the image obtained by the imaging device 220; analyze the image and determine the pixels having the wanted cells being captured therein and the pixels having the unwanted cells being captured therein; and in response to determining the pixels having the unwanted cells being captured therein, control the cell manipulation panel 210 to release the unwanted cells to the fluid medium.

Figure 5A:
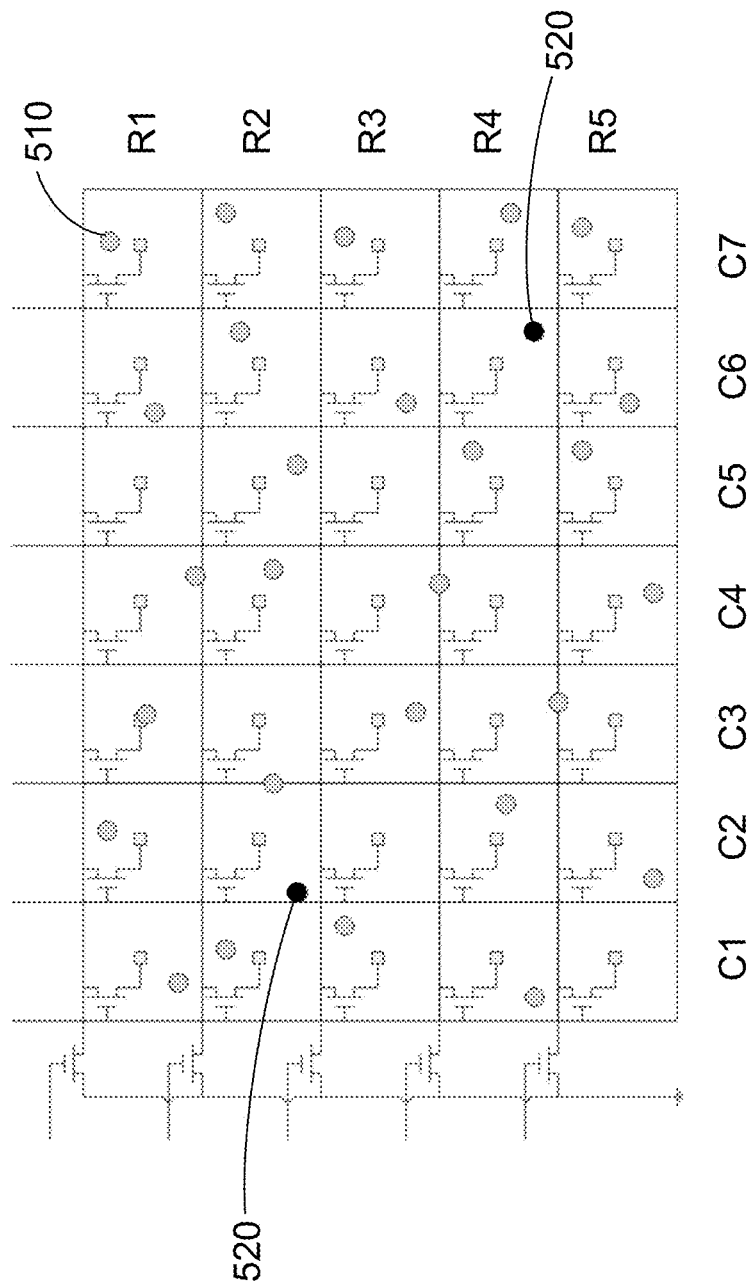
FIGS. 5A-5D schematically show a process of capturing and releasing cells using a cell manipulation panel according to one embodiment of the present disclosure, where unwanted cells are respectively released.
Figure 5B:
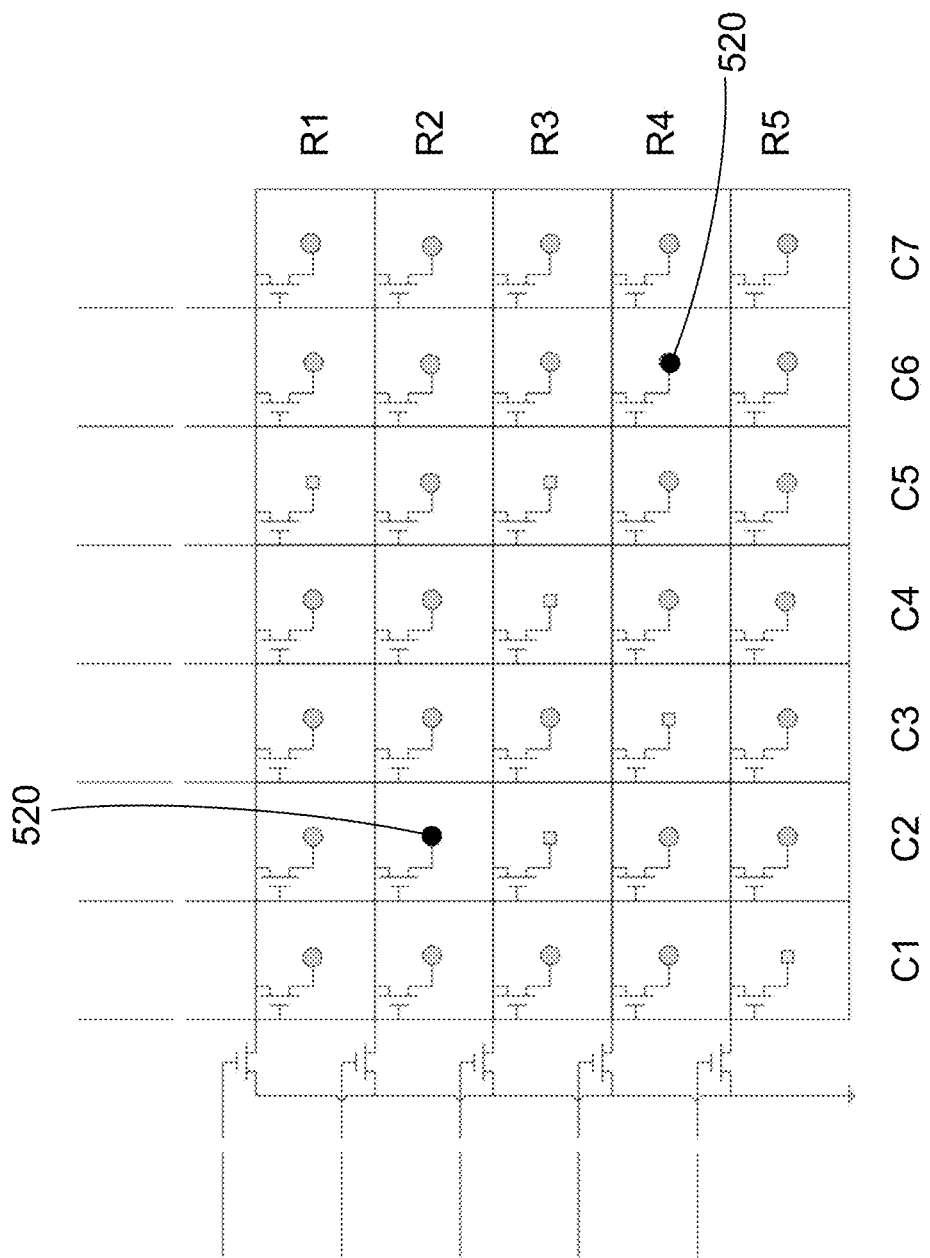
Figure 5C:
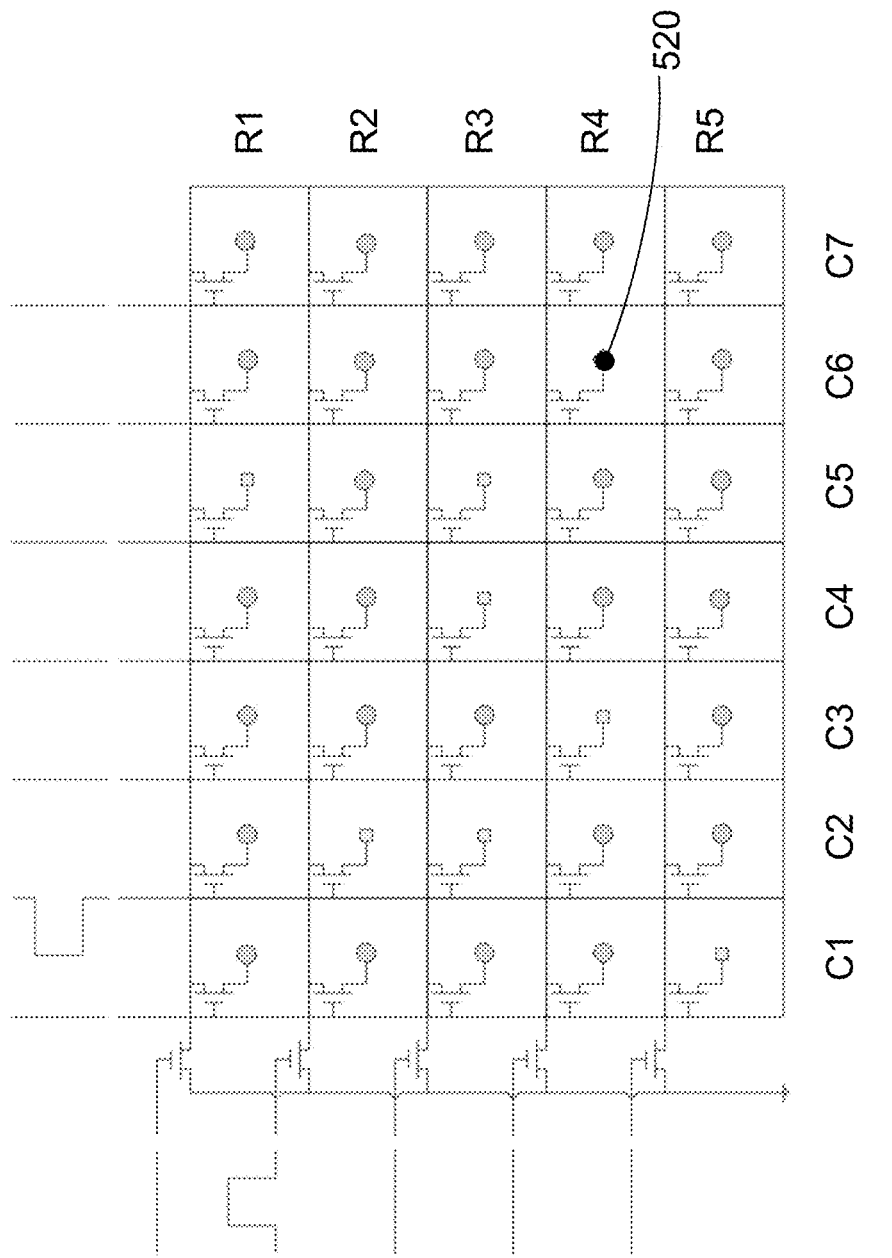
Figure 5D:
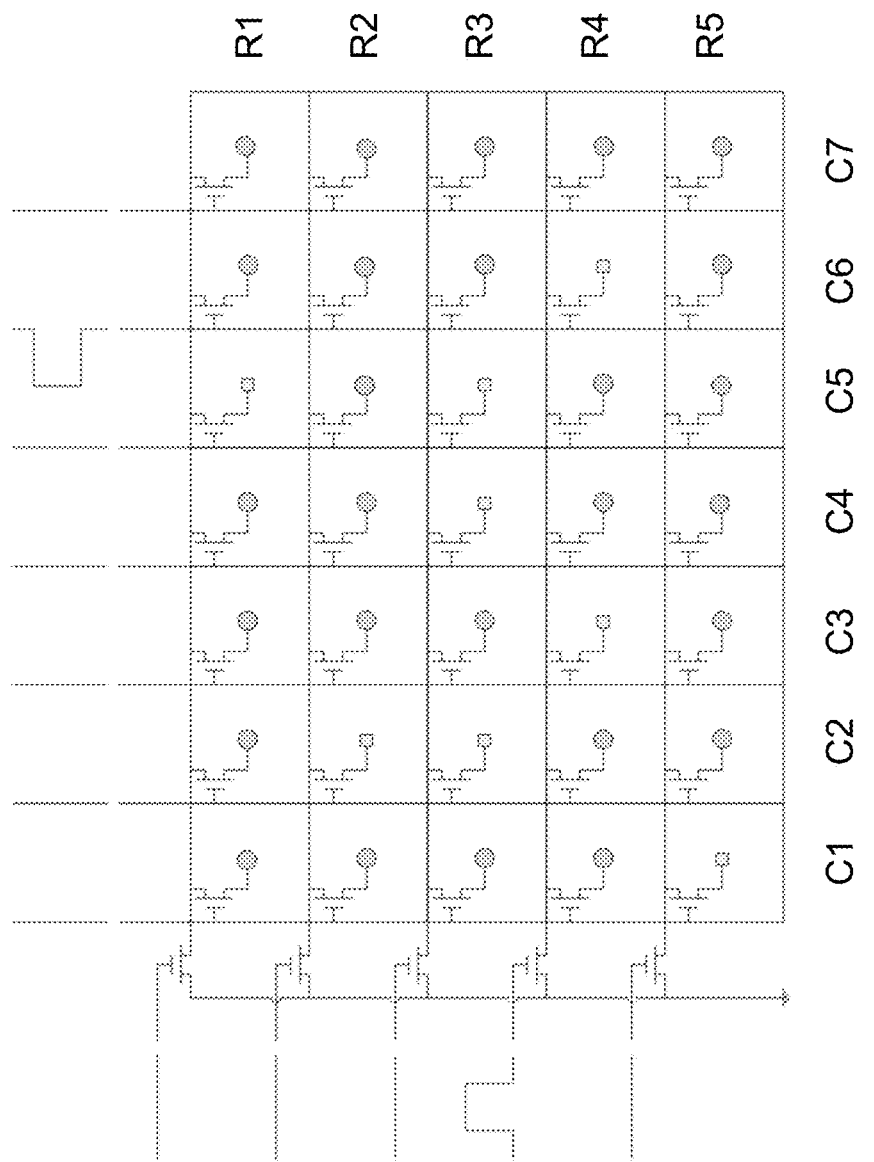

FIGS. 5A-5D schematically show a process of capturing and releasing cells using a cell manipulation panel according to one embodiment of the present disclosure. Specifically, for description purposes, the pixels in each of FIGS. 5A-5D are labeled using the columns C1-C7 and the rows R1-R5. For example, the pixel in row R1 and column C1 is labeled as the pixel (R1C1). Further, the cells include multiple wanted cells 510 (shown as gray dots) and two unwanted cells 520 (shown as solid black dots). When the cell manipulation panel is not in the operational mode, as shown in FIG. 5A, no voltage is applied, and there is no DEP force. In this case, the cells (including wanted cells 510 and unwanted cells 520) exist in the fluid medium and are not captured by the pixels. When the cell manipulation panel is turned on to the operational mode, as shown in FIG. 5B, all the first gate signals and all the second gate signals are low signals VL (i.e., the OFF signals), such that each pixel correspondingly captures a cell in its via. In this case, since the unwanted cells 520 are lightened, these unwanted cells 520 may be identified by the controller in analyzing the image captured by the imaging device. For example, as shown in FIG. 5B, the controller may determine, based on analyzing the image captured by the imaging device, that the cells captured at the pixels (R2C2) and (R4C6) are unwanted cells. Once the unwanted cells 520 are identified, the unwanted cells may be released respectively. For example, as shown in FIG. 5C, the first gate signal provided by the first gate line corresponding to the column C2 and the second gate signal provided by the second gate line corresponding to the row R2 are switched to high signals VH (i.e., the ON signal), thus releasing the unwanted cell 520 at the pixel (R2C2). Then, as shown in FIG. 5D, the first gate signal provided by the first gate line corresponding to the column C2 and the second gate signal provided by the second gate line corresponding to the row R2 are switched back to the low signals VL (i.e., the OFF signal), and the first gate signal provided by the first gate line corresponding to the column C6 and the second gate signal provided by the second gate line corresponding to the row R4 are switched to the high signals VH (i.e., the ON signal), thus releasing the unwanted cell 520 at the pixel (R4C6). In this case, all of the cells remained captured by the pixels are wanted cells 510, and all the unwanted cells 520 are released, thus isolating the wanted cells 510 from the unwanted cells 520.

Figure 6A:
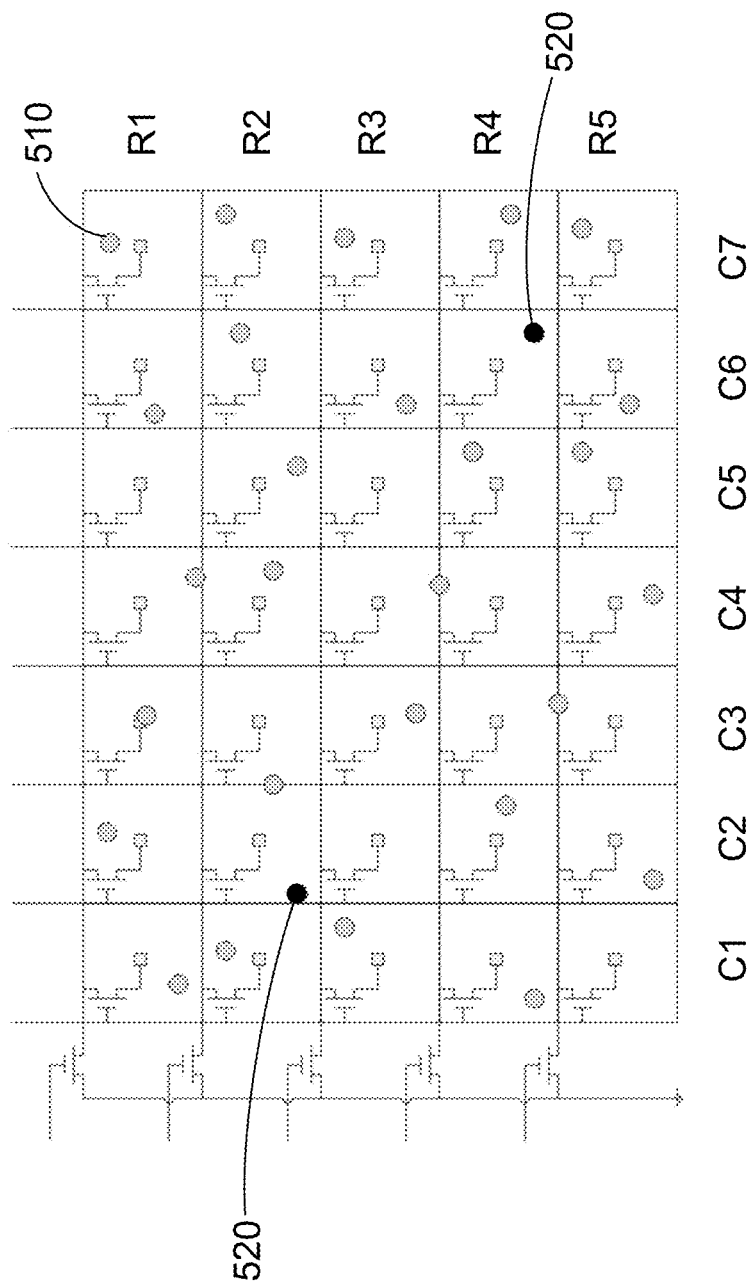
FIGS. 6A-6F schematically show a process of capturing and releasing cells using a cell manipulation panel according to one embodiment of the present disclosure, where unwanted cells are sequentially released.
Figure 6B:
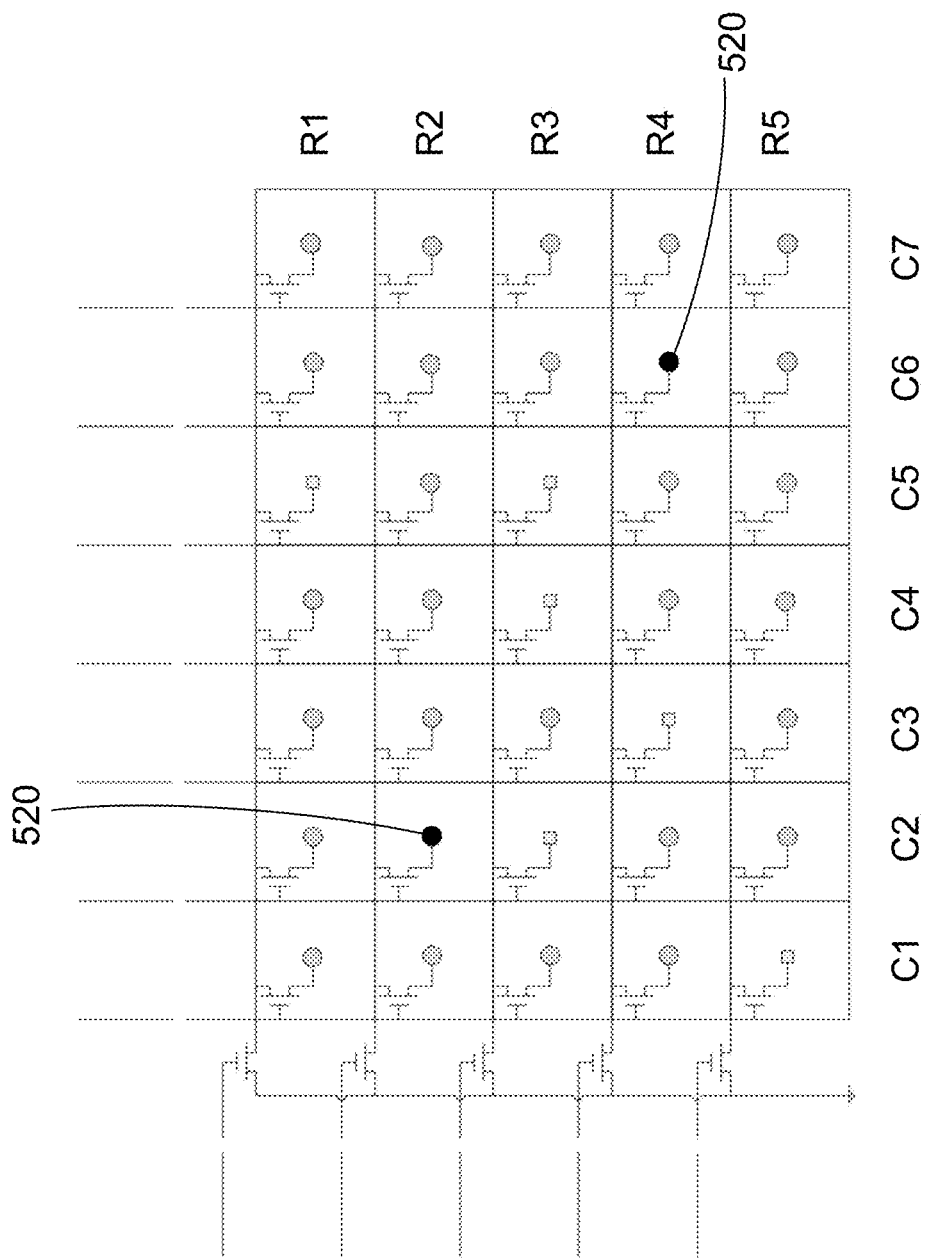
Figure 6C:
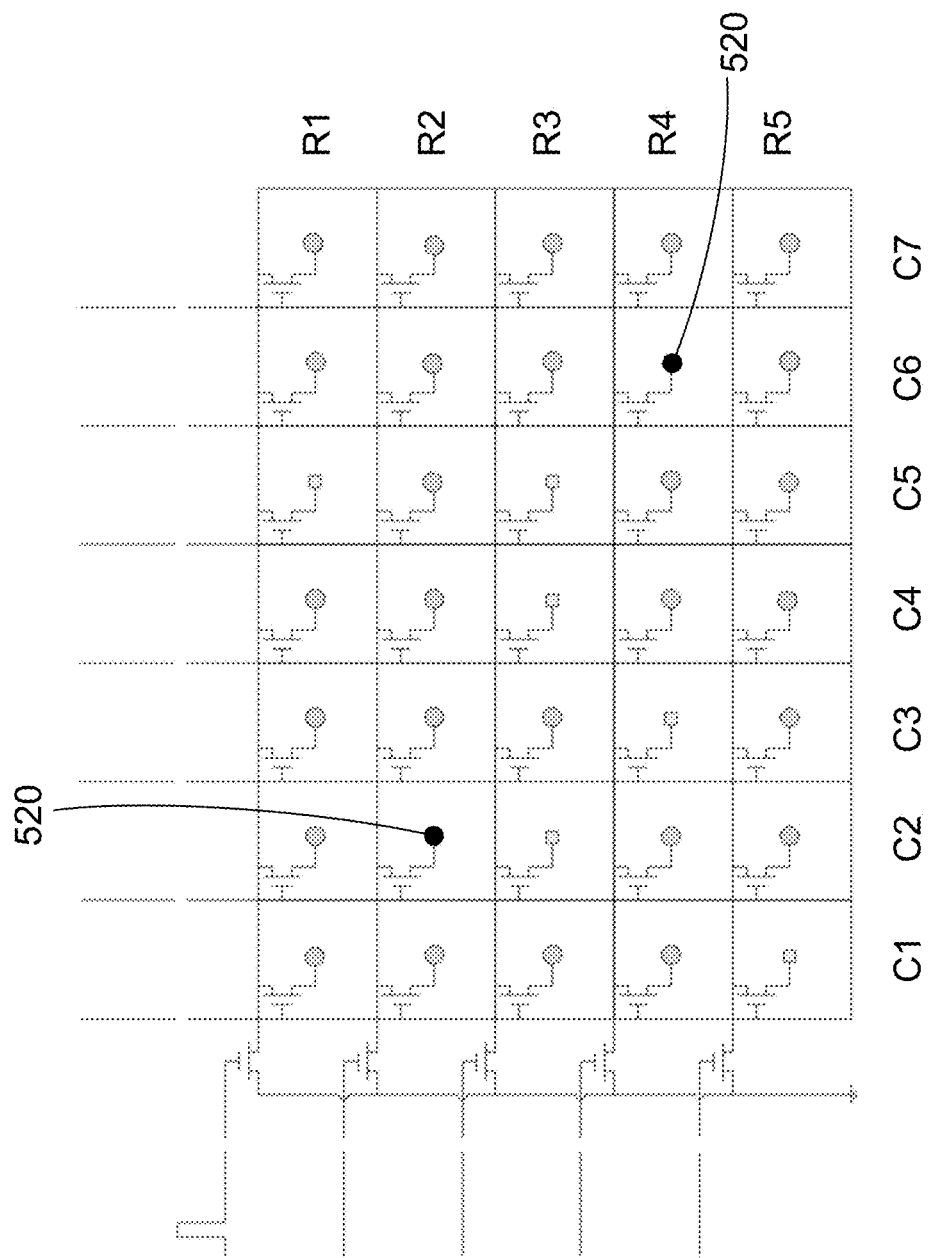
Figure 6D:
Figure 6E:
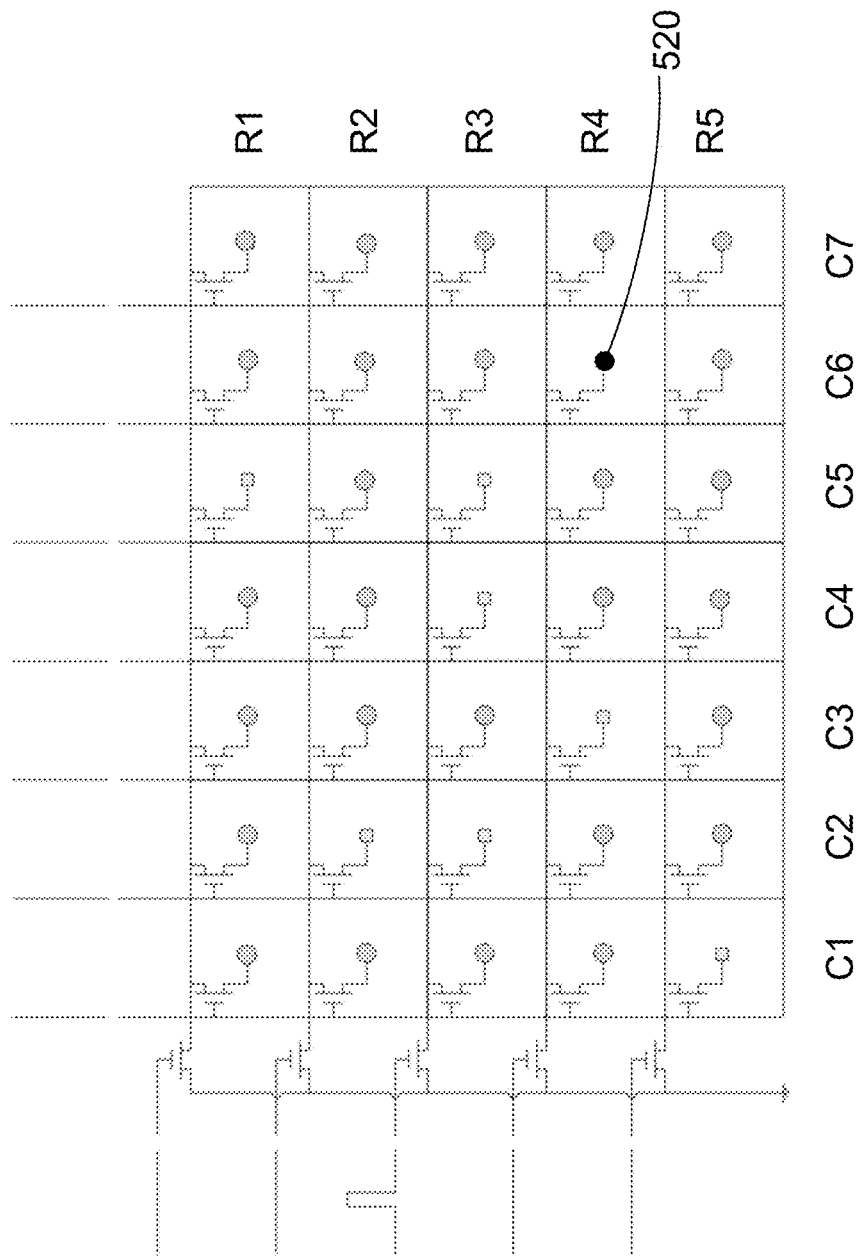
Figure 6F:
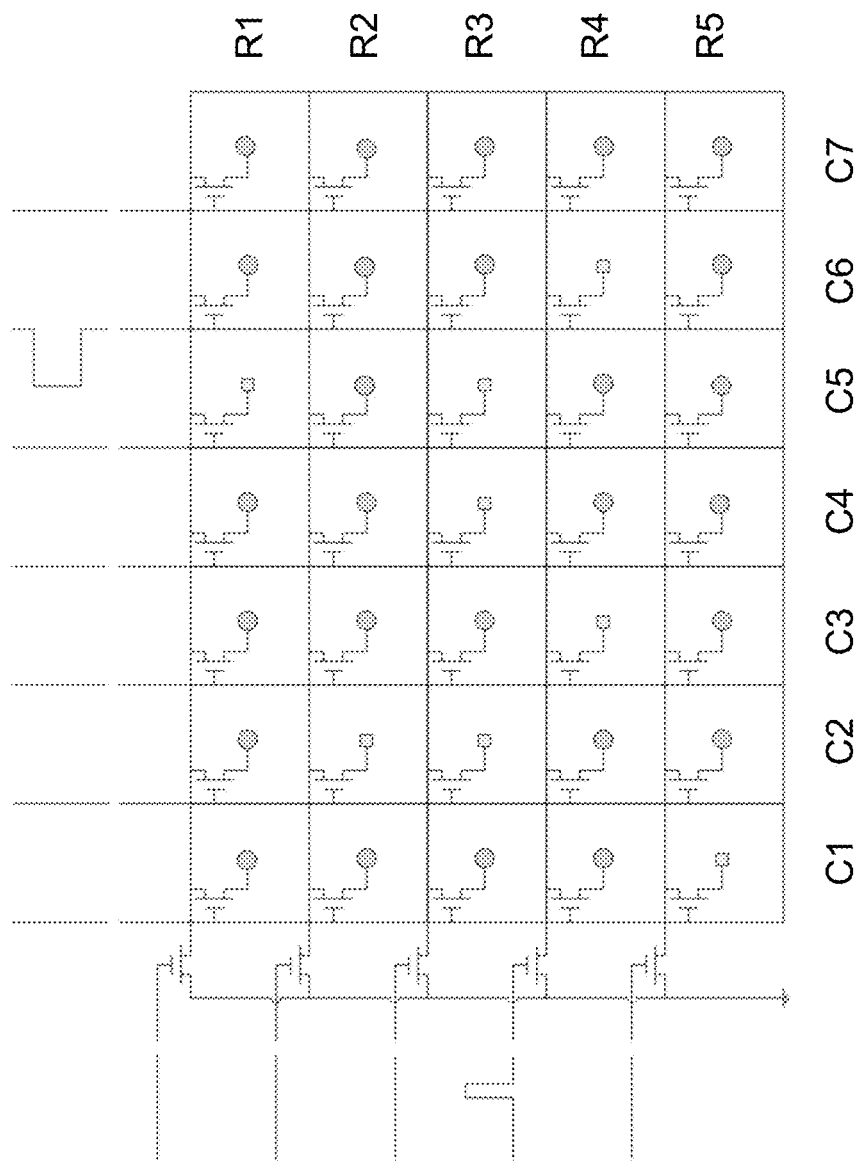

In the exemplary embodiment as shown in FIGS. 5A-5D, the unwanted cells 520 are respectively released. In certain embodiments, it is also possible to release the unwanted cells 520 sequentially. For example, FIGS. 6A-6F schematically show a process of capturing and releasing cells using a cell manipulation panel according to one embodiment of the present disclosure, where unwanted cells are sequentially released. Specifically, for description purposes, the pixels in each of FIGS. 6A-6F are labeled similarly using the columns C1-C7 and the rows R1-R5. For example, the pixel in row R1 and column C1 is labeled as the pixel (R1C1). Further, the cells include multiple wanted cells 510 (shown as gray dots) and two unwanted cells 520 (shown as solid black dots). When the cell manipulation panel is not in the operational mode, as shown in FIG. 6A, no voltage is applied, and there is no DEP force. In this case, the cells (including wanted cells 510 and unwanted cells 520) exist in the fluid medium and are not captured by the pixels. When the cell manipulation panel is turned on to the operational mode, as shown in FIG. 5B, all the first gate signals and all the second gate signals are low signals VL (i.e., the OFF signals), such that each pixel correspondingly captures a cell in its via. In this case, since the unwanted cells 520 are lightened, these unwanted cells 520 may be identified by the controller in analyzing the the image captured by the imaging device. For example, as shown in FIG. 6B, unwanted cells 520 are captured at the pixels (R2C2) and (R4C6). Once the unwanted cells 520 are identified, the unwanted cells may be released sequentially. For example, as shown in FIG. 6C, the second gate signal provided by the second gate line corresponding to the row R1 is switched to the high signal VH (i.e., the ON signal). However, there is no unwanted cell 520 in any of the pixels in the row R1, and all first gate signals remain low signals VL (i.e., the OFF signals), such that no cell in the row R1 is released. Then, as shown in FIG. 6D, the second gate signal provided by the second gate line corresponding to the row R1 is switched back to the low signal VL (i.e., the OFF signal), and the second gate signal provided by the second gate line corresponding to the row R2 is switched to the high signal VH (i.e., the ON signal). In this case, since there is an unwanted cell 520 in the pixel (R2C2), the first gate signal provided by the first gate line corresponding to the column C2 is also switched to the high signal VH (i.e., the ON signal), thus releasing the unwanted cell 520 at the pixel (R2C2). Subsequently, as shown in FIG. 6E, the second gate signal provided by the second gate line corresponding to the row R2 is switched back to the low signal VL (i.e., the OFF signal), and the second gate signal provided by the second gate line corresponding to the row R3 is switched to the high signal VH (i.e., the ON signal). However, there is no unwanted cell 520 in any of the pixels in the row R3, and all first gate signals remain or switch back to the low signals VL (i.e., the OFF signals), such that no cell in the row R3 is released. Then, as shown in FIG. 6F, the second gate signal provided by the second gate line corresponding to the row R3 is switched back to the low signal VL (i.e., the OFF signal), and the second gate signal provided by the second gate line corresponding to the row R4 is switched to the high signal VH (i.e., the ON signal). In this case, since there is another unwanted cell 520 in the pixel (R4C6), the first gate signal provided by the first gate line corresponding to the column C6 is also switched to the high signal VH (i.e., the ON signal), thus releasing the unwanted cell 520 at the pixel (R4C6). Similarly, the second gate signals provided by the second gate lines corresponding to the subsequent rows are correspondingly switched to the high signal VH (i.e., the ON signal) in a sequential order through the rows, and all the unwanted cells 520 may be released sequentially. In this case, all of the cells remained captured by the pixels are wanted cells 510, and all the unwanted cells 520 are released, thus isolating the wanted cells 510 from the unwanted cells 520.

In the embodiments as described above, cell isolation is performed to isolate the wanted cells 510 from the unwanted cells 520. In certain embodiments, other types of cell manipulation may be performed. In one embodiment, for example, cell purification may be performed by capturing the wanted cells 510 and releasing the unwanted cells 520 back to the fluid medium, such that the ratio of the unwanted cells 520 to the wanted cells 510 in the fluid medium would increase, thus purifying the unwanted cells 520 in the fluid medium.

Figure 7A:
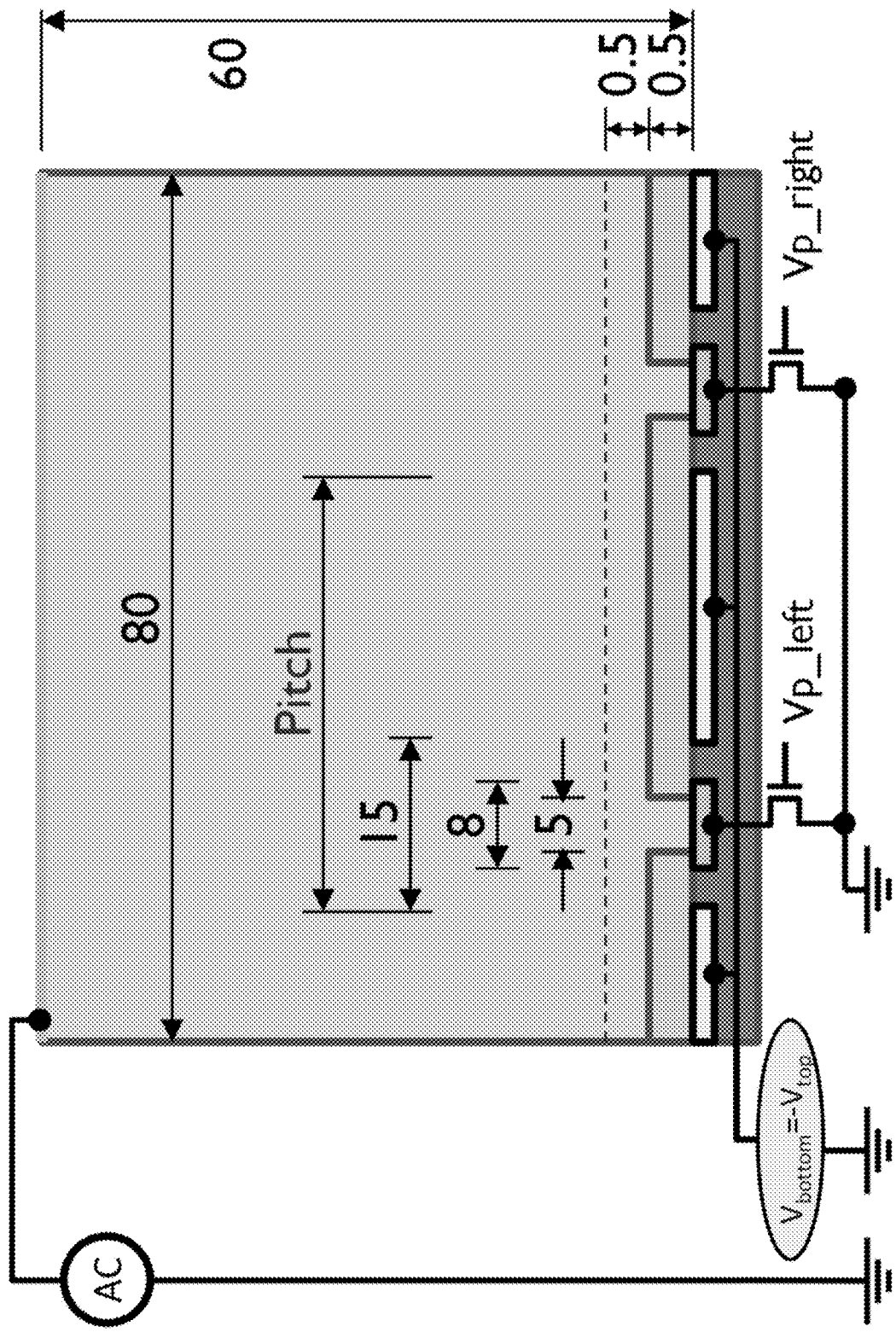
FIG. 7A schematically shows a cross-sectional view of a simulation model of the cell manipulation panel having two adjacent pixels according to one embodiment of the present disclosure.
Figure 7B:
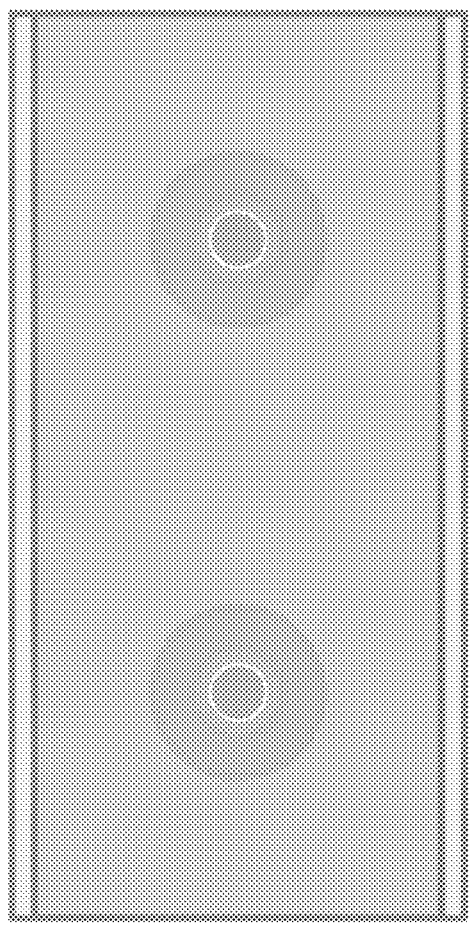
FIG. 7B schematically shows a top view of the simulation model as shown in FIG. 7A.

The inventors have performed simulation to the cell manipulation panel as discussed above using a simulation model with certain dimensions. FIGS. 7A and 7B schematically show a simulation model of the cell manipulation panel having two adjacent pixels according to one embodiment of the present disclosure. As shown in FIG. 7A, the simulation model is a simplified cell manipulation panel with two adjacent pixels, with only 1 insulating layer being provided, the fluid medium being water, and the cell particles being red blood cells. The common voltage $V_{COM}$ ($=V_{top}$) is set as +10V, and the bottom voltage $V_{bottom}$ is set as −10V, which is the inverse of the common voltage. The 2 voltage signals Vp_left and Vp_right being provided to the first gate electrodes of the first TFTs of the two pixels are both set to be OFF. Meanwhile, the pitch distance between the pixels are set to be 50, 40, 35, 30 and 20 um, respectively. In all cases, the fluid velocity of the fluid medium remains 0 (i.e., the fluid medium is not flowing). Table 1 shows the material properties of the simulation.

TABLE 1

| | Fluid Medium (water) | Insulator ($Si_3N_4$) | Cell Particle (Red Blood Cell) |
|---|---|---|---|
| Electrical conductivity [S/m] | 1 | 1e−14 | 0.31 |
| Relative permittivity | 80 | 6.9 | 59 |
| Density [kg/m$^3$] | 1000 | 3950 | 1050 |
| Others | Dynamic viscosity = 1e−3 [Pa*s] | Thickness = 0.5 um | Diameter = 5 um |

Figure 7C:
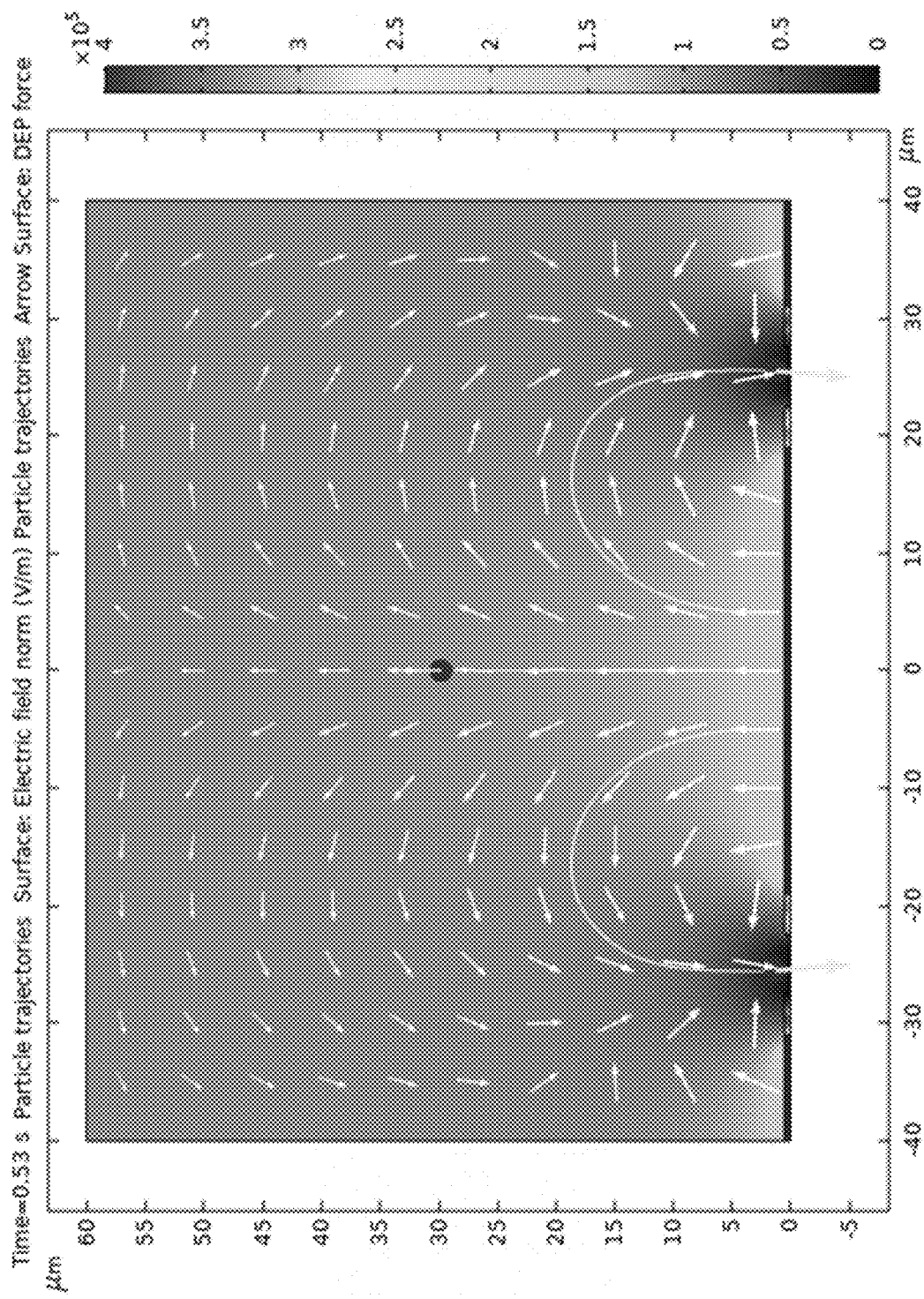
FIG. 7C shows the simulation result of the simulation model as shown in FIG. 7A, where the pitch distance is 50 um and the time is 0.53 s.
Figure 7D:
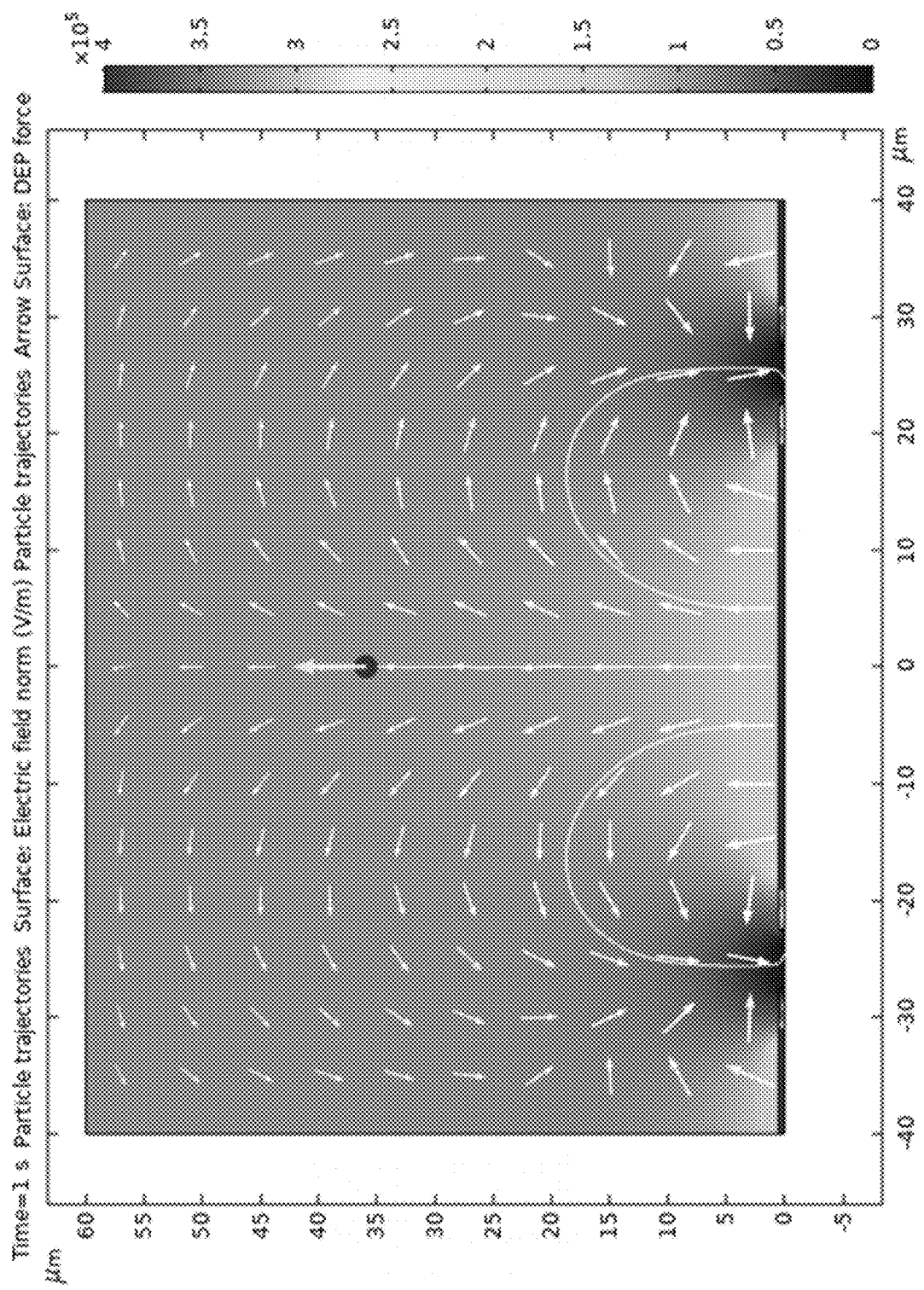
FIG. 7D shows the simulation result of the simulation model as shown in FIG. 7A, where the pitch distance is 50 um and the time is 1 s.

FIGS. 7C and 7D show the simulation result of the simulation model as shown in FIGS. 7A and 7B, where the pitch distance is 50 um. Specifically, 3 red blood cells are released initially at the locations (−5. 2.5), (0, 2.5) and (5, 2.5), and the white arrows show the DEP forces distribution. At the time t=0.53 s (see FIG. 7C), the 2 red blood cells at the outer sides are captured by the vias. In comparison, the red blood cell at the center keeps moving upward at both t=0.53 s (FIG. 7C) and t=1 s (FIG. 7D), and appears to in the trend of moving upward until it reaches the top of the cell gap.

Figure 7E:
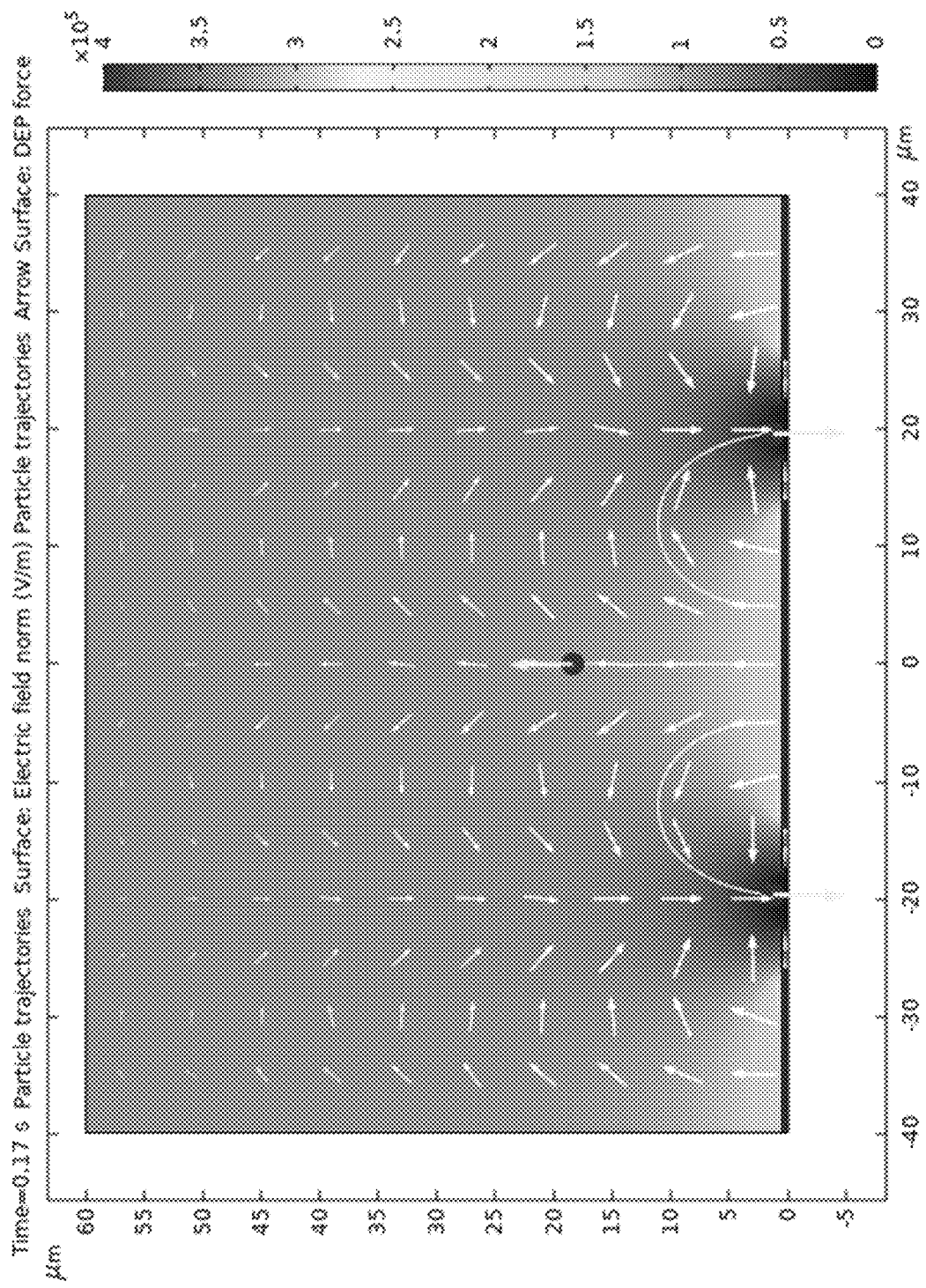
FIG. 7E shows the simulation result of the simulation model as shown in FIG. 7A, where the pitch distance is 40 um and the time is 0.17 s.
Figure 7F:
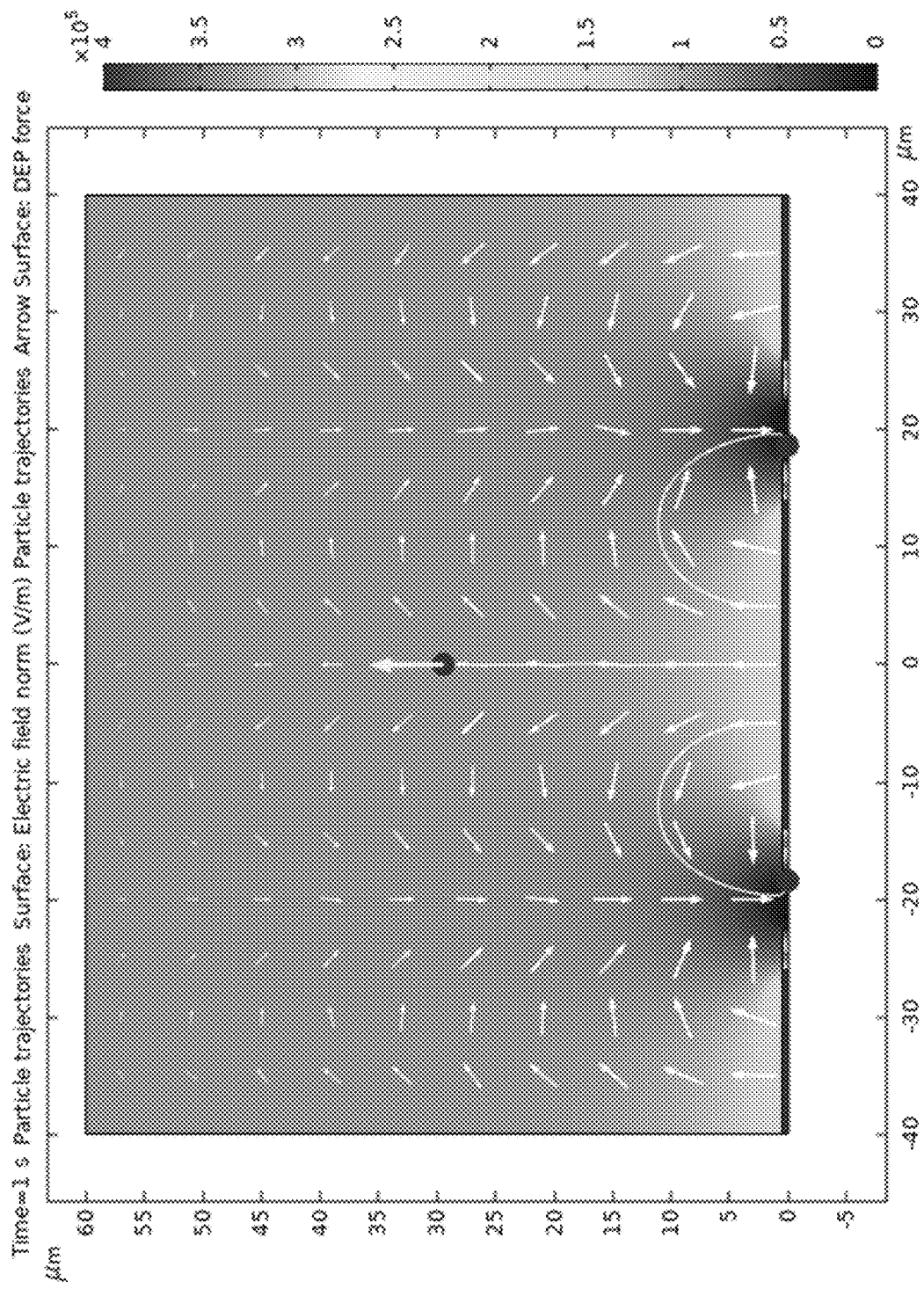
FIG. 7F shows the simulation result of the simulation model as shown in FIG. 7A, where the pitch distance is 40 um and the time is 1 s.

FIGS. 7E and 7F show the simulation result of the simulation model as shown in FIGS. 7A and 7B, where the pitch distance is 40 um. Specifically, 3 red blood cells are released initially at the locations (−5. 2.5), (0, 2.5) and (5, 2.5), and the white arrows show the DEP forces distribution. At the time t=0.17 s (see FIG. 7E), the 2 red blood cells at the outer sides are captured by the vias. In comparison, the red blood cell at the center keeps moving upward at both t=0.17 s (FIG. 7E) and t=1 s (FIG. 7F), and appears to in the trend of moving upward until it reaches the top of the cell gap.

Figure 7G:
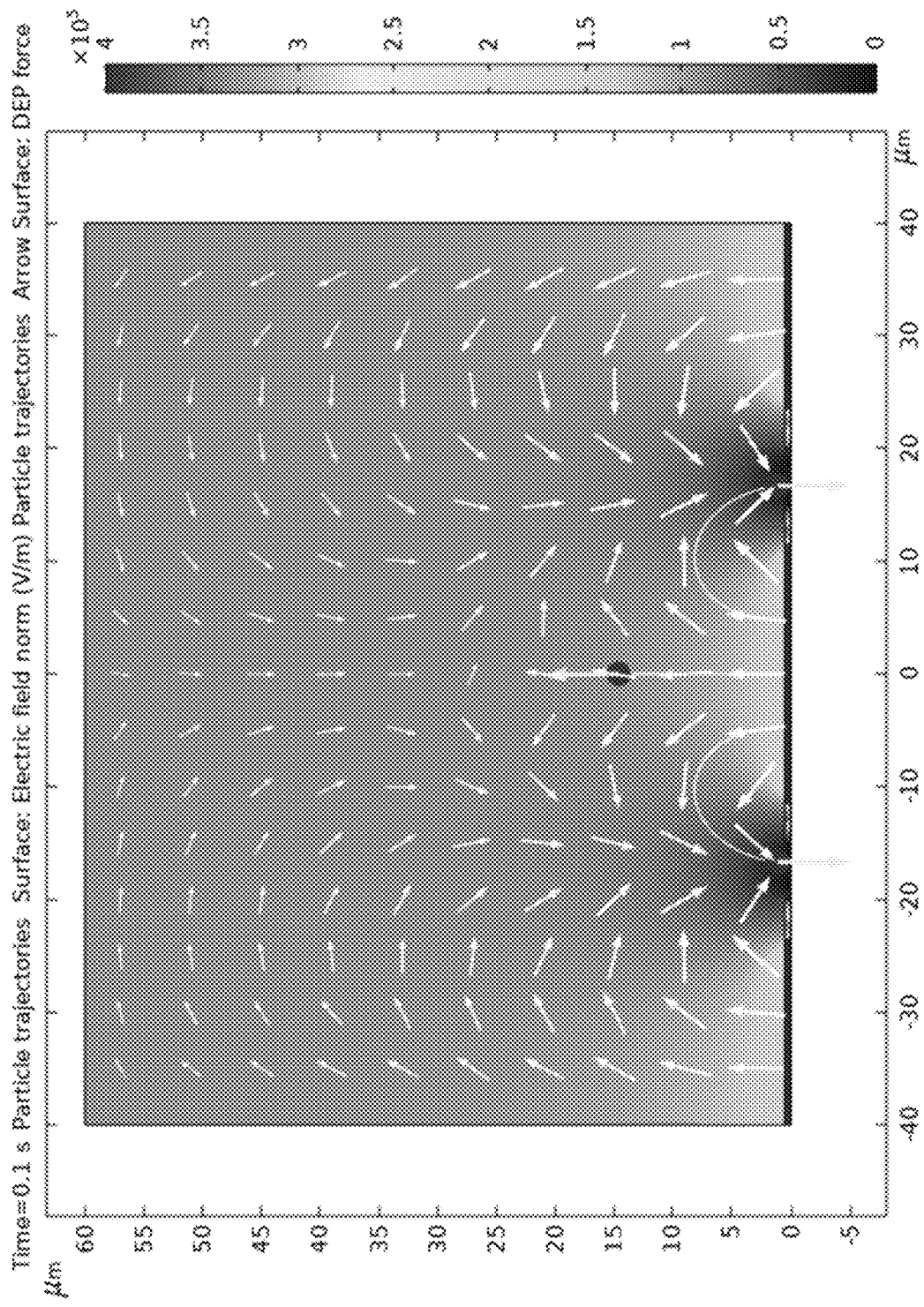
FIG. 7G shows the simulation result of the simulation model as shown in FIG. 7A, where the pitch distance is 35 um and the time is 0.1 s.
Figure 7H:
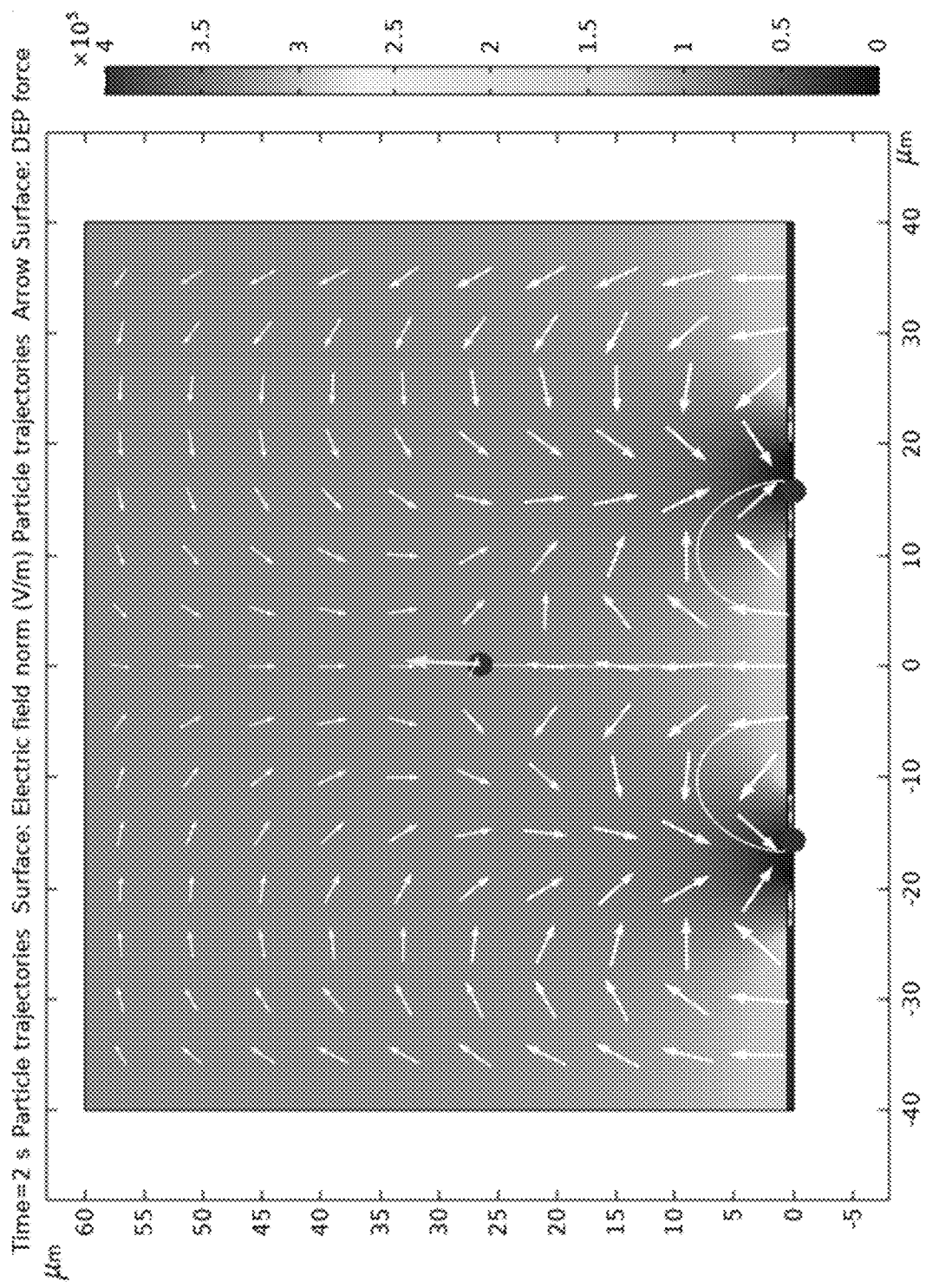
FIG. 7H shows the simulation result of the simulation model as shown in FIG. 7A, where the pitch distance is 35 um and the time is 2 s.

FIGS. 7G and 7H show the simulation result of the simulation model as shown in FIGS. 7A and 7B, where the pitch distance is 35 um. Specifically, 3 red blood cells are released initially at the locations (−5. 2.5), (0, 2.5) and (5, 2.5), and the white arrows show the DEP forces distribution. The difference between this model and the previous ones exists in that the DEP forces at the center of the model do not move upward to the top of the cell gap. Instead, at the height of 30 um, the DEP forces at the center of model start moving downward. At the time t=0.1 s (see FIG. 7G), the 2 red blood cells at the outer sides are captured by the vias. In comparison, the red blood cell at the center keeps moving upward until about t=1.5 s, and at t=2 s (FIG. 7H), the red blood cell almost remain at the same location without a slight rotation to the right. Based on the DEP force distribution, it appears that the red blood cell at the center may eventually be captured by one of the vias.

Figure 7I:
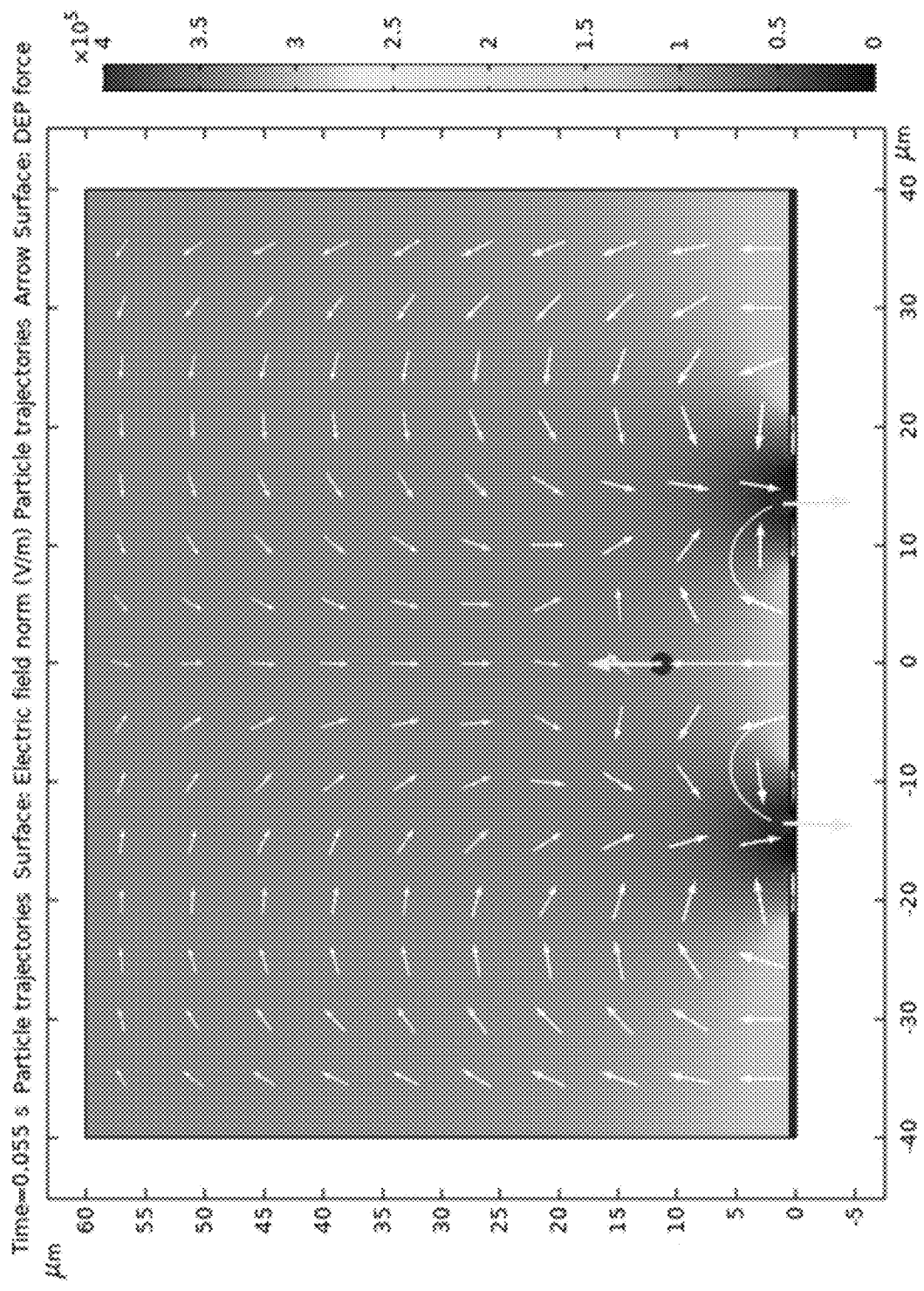
FIG. 7I shows the simulation result of the simulation model as shown in FIG. 7A, where the pitch distance is 30 um and the time is 0.055 s.
Figure 7J:
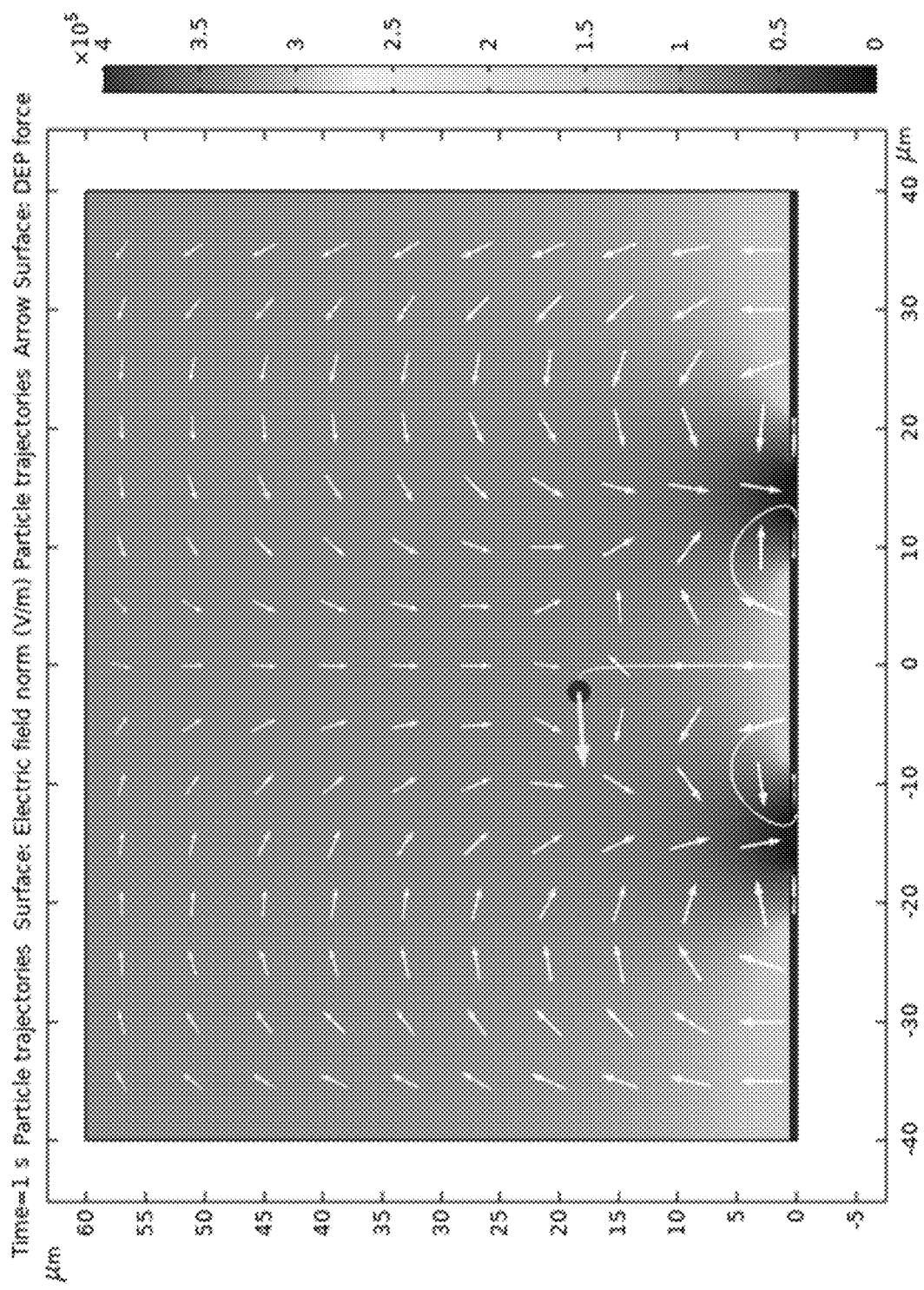
FIG. 7J shows the simulation result of the simulation model as shown in FIG. 7A, where the pitch distance is 30 um and the time is 1 s.

FIGS. 7I and 7J show the simulation result of the simulation model as shown in FIGS. 7A and 7B, where the pitch distance is 30 um. Specifically, 3 red blood cells are released initially at the locations (−5. 2.5), (0, 2.5) and (5, 2.5), and the white arrows show the DEP forces distribution. The difference between this model and the previous ones exists in that the DEP forces at the center of the model do not move upward to the top of the cell gap. Instead, at the height of 17.5 um, the DEP forces at the center of model start moving downward. At the time t=0.055 s (see FIG. 7I), the 2 red blood cells at the outer sides are captured by the vias. Further, at the time t=1 s (see FIG. 7J), the red blood cell at the center starts moving leftward. Based on the DEP force distribution, it appears that the red blood cell at the center may eventually be captured by one of the vias.

Figure 7K:
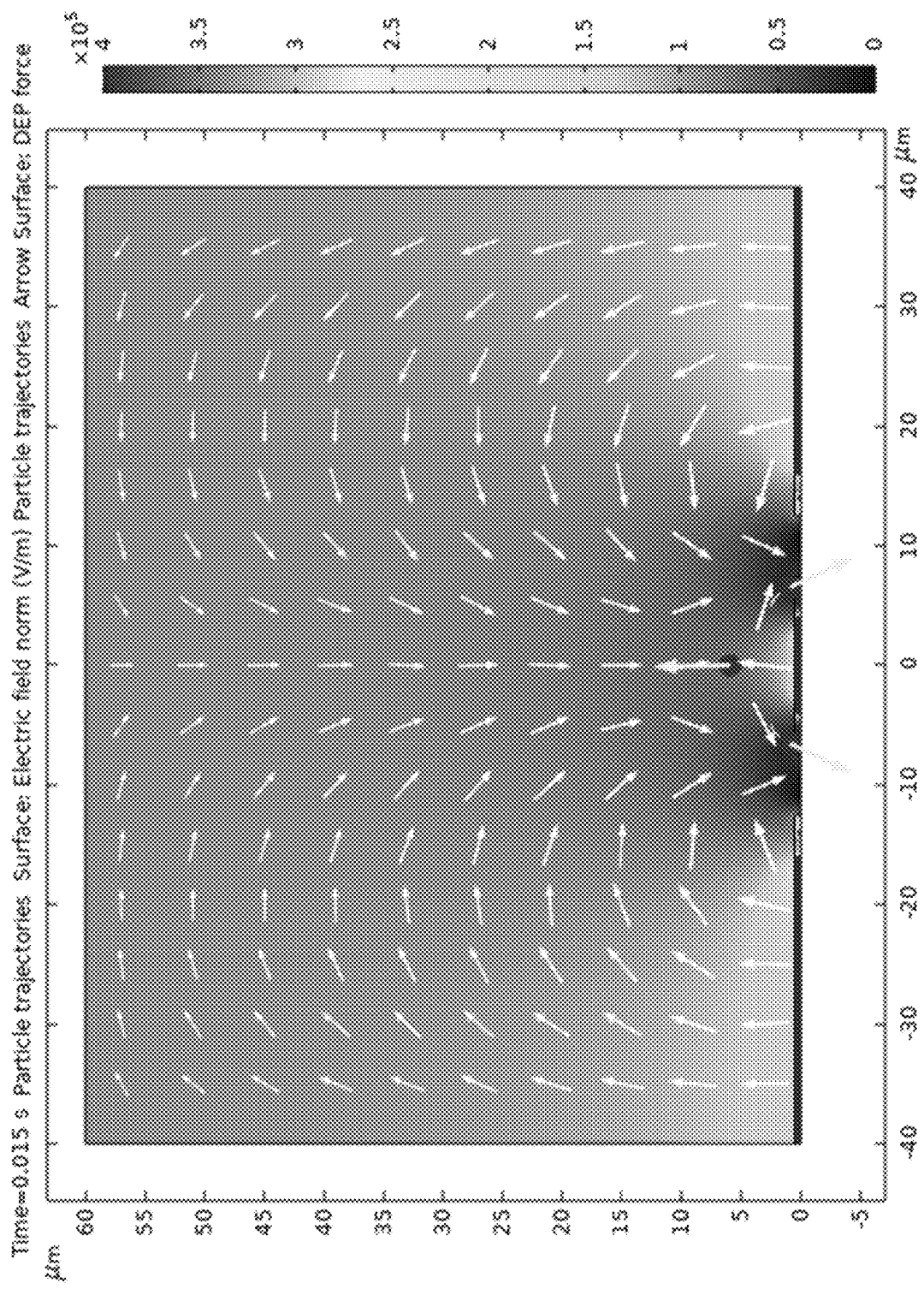
FIG. 7K shows the simulation result of the simulation model as shown in FIG. 7A, where the pitch distance is 20 um and the time is 0.015 s.
Figure 7L:
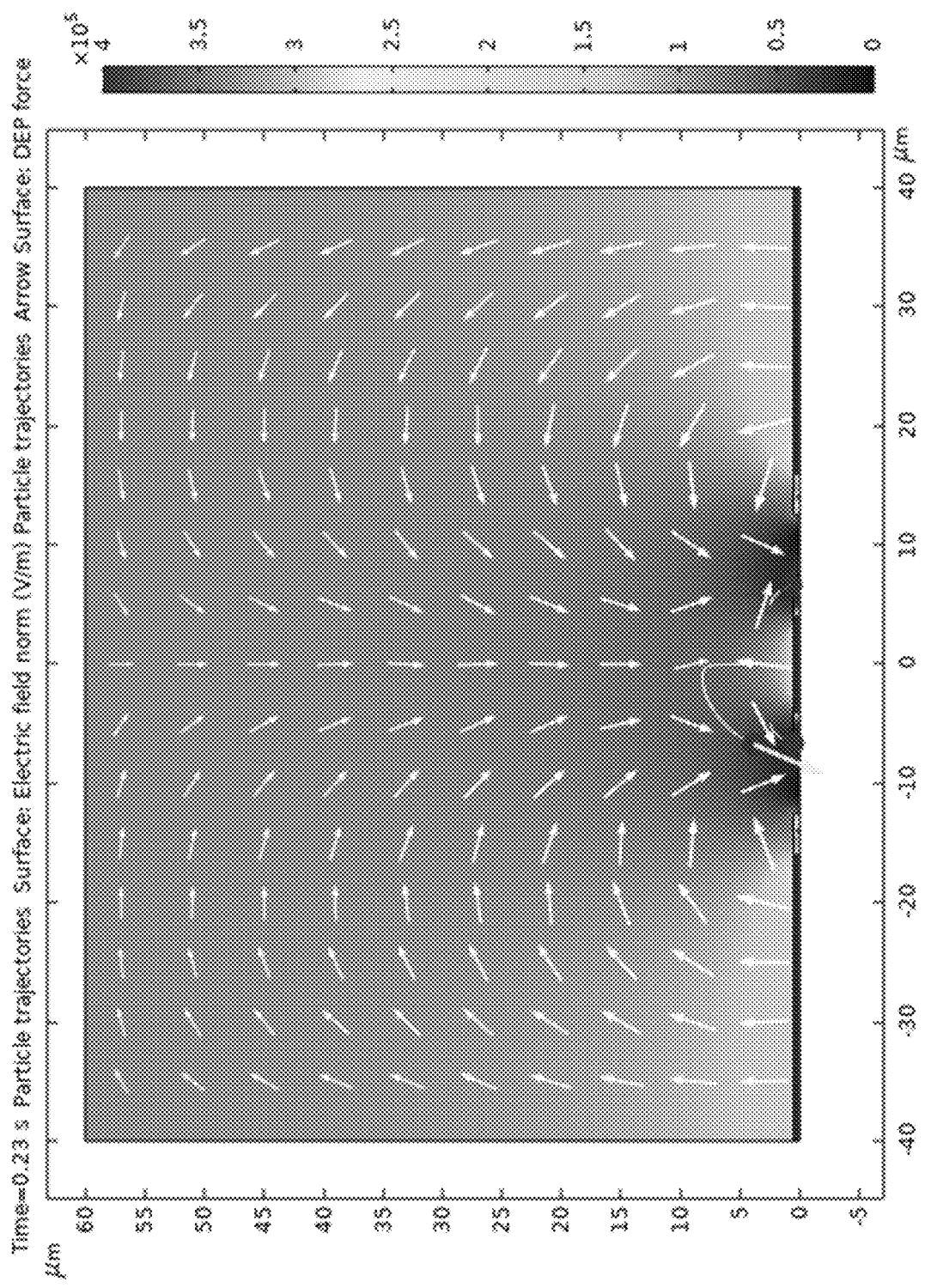
FIG. 7L shows the simulation result of the simulation model as shown in FIG. 7A, where the pitch distance is 20 um and the time is 0.23 s.

FIGS. 7K and 7L show the simulation result of the simulation model as shown in FIGS. 7A and 7B, where the pitch distance is 20 um. Specifically, 3 red blood cells are released initially at the locations (−5. 2.5), (0, 2.5) and (5, 2.5), and the white arrows show the DEP forces distribution. The difference between this model and the previous ones exists in that the DEP forces at the center of the model do not move upward to the top of the cell gap. Instead, at the height of 5 um, the DEP forces at the center of model start moving downward. At the time t=0.015 s (see FIG. 7K), the 2 red blood cells at the outer sides are captured by the vias. Further, at the time t=0.23 s (see FIG. 7L), the red blood cell at the center has moved leftward, and is located very close to the via at the left. Thus, it appears that the red blood cell at the center may also be captured by via at the left.

Based on the simulation results, it appears that the red blood cells being located near the vias will be captured by the vias once the cell manipulation panel starts in the operational mode. When the pitch distance is relatively large, the DEP forces at the center area between the two vias have a trend of moving upward. In comparison, when the pitch distance is reduced, the DEP forces are increased. In the cases of the pitch distance being 40-50 um, the upward DEP forces at the center area may reach the top of the cell gap, allowing the red blood cell in this center area to move upward to reach the top of the cell gap. In this case, the fluid medium may flow and take away the excess red blood cells. In comparison, when the pitch distance is reduced to be 35 um or shorter, the upward DEP forces at the center area do not reach the top of the cell gap, and may stop at a certain location or rotate and turn toward one of the vias.

Figure 8:
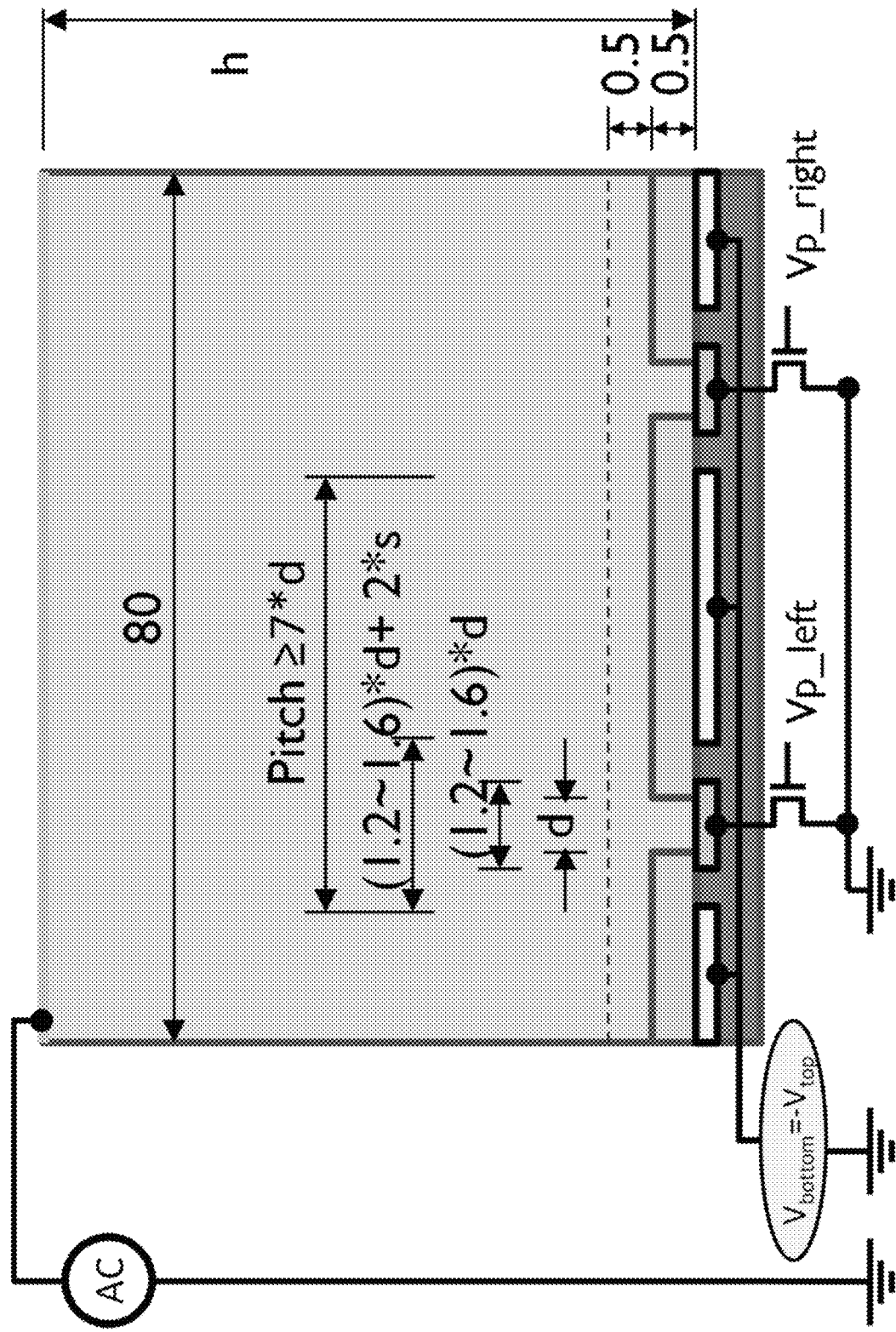
FIG. 8 schematically shows a cross-sectional view of a modified model of the cell manipulation panel having two adjacent pixels according to one embodiment of the present disclosure.

In certain embodiments, a modified model of the cell manipulation panel may be provided based on the simulation results as described above. For example, FIG. 8 schematically shows a cross-sectional view of a modified model of the cell manipulation panel having two adjacent pixels according to one embodiment of the present disclosure. As shown in FIG. 8, for each via having the diameter d, the cells to be captured may have a cell diameter less than d. The portion of the second electrode below the via may have a diameter in the range of (1.2~1.6) *d. A circumferential width s of the insulating layer may exist at the peripheral area around the via, and based on the typical liquid crystal display (LCD) manufacturing process, the circumferential width s may be in the range of 2-3 um. In certain embodiments, the pitch distance may be set to be 7*d or greater, such that the cells being located near the vias will be captured by the vias, and the excessive cells away from the vias may move upward to reach the top of the cell gap and be taken away by the fluid medium. Further, the height h of the cell gap (which functions as the passage of the fluid medium) may be determined by the following equation:

$$h = \Delta V / X \quad (9)$$

Specifically, when the common voltage is 10V and the bottom voltage is 0V, an average electric field generated is 0.167 [=(10−0)/60] V/um, and when the common voltage is 10V and the bottom voltage is −10V, an average electric field generated is 0.333 [=(10+100)/60] V/um. In other words, X can be in a range of 0.16~70.333.

Figure 9:
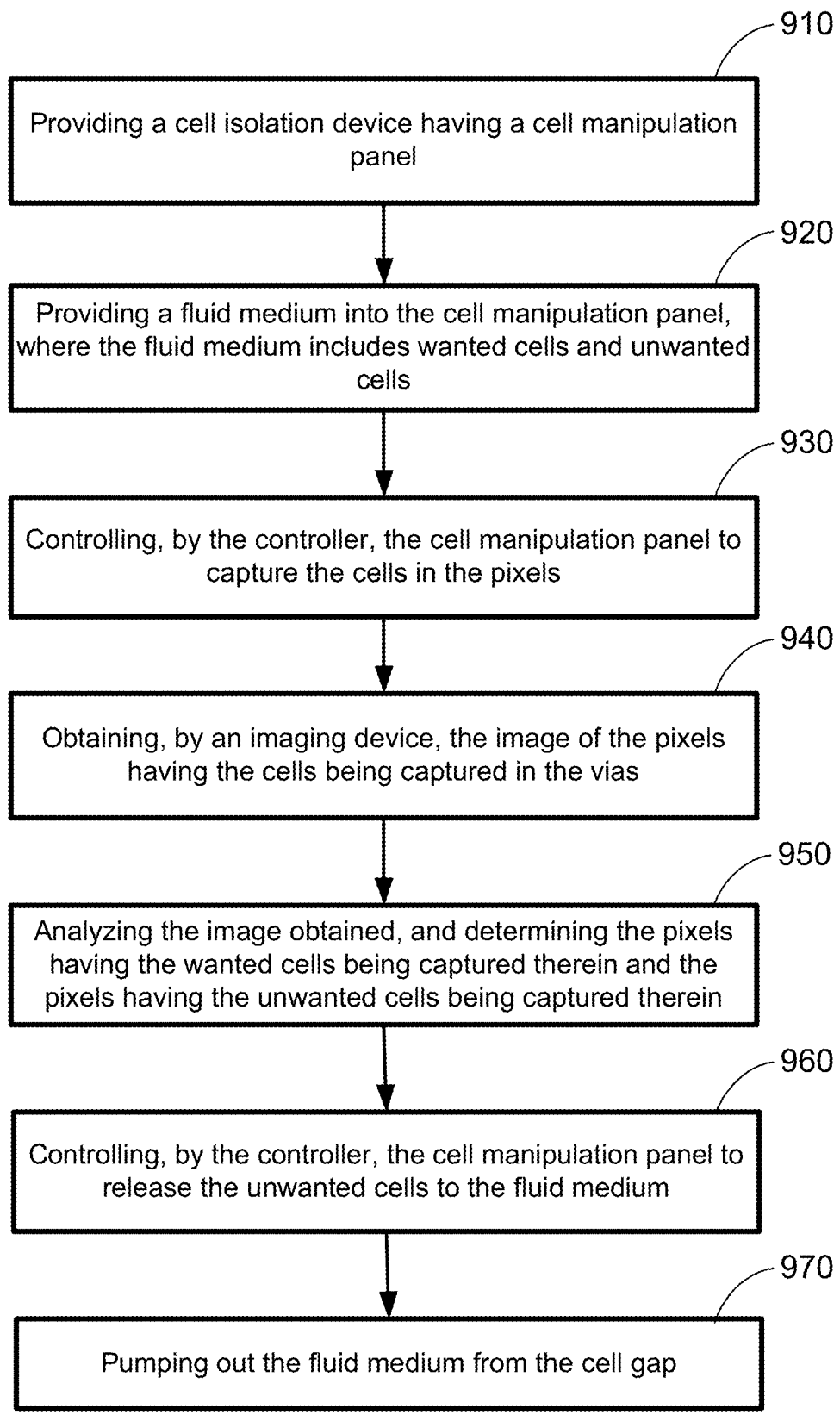
FIG. 9 shows a flowchart of a method of performing cell manipulation according to certain embodiments of the present disclosure.

In another aspect of the present disclosure, a method of performing cell manipulation is provided. For example, FIG. 9 shows a flowchart of a method of performing cell manipulation according to certain embodiments of the present disclosure. Specifically, the method as shown in FIG. 9 may be implemented on the cell isolation device as shown in FIG. 2 with a cell manipulation panel as shown in FIGS. 3 and 4. It should be particularly noted that, unless otherwise stated in the disclosure, the steps of the method may be arranged in a different sequential order, and are thus not limited to the sequential order as shown in FIG. 9.

As shown in FIG. 9, at procedure 910, a cell isolation device having a cell manipulation panel is provided. At procedure 920, a fluid medium is provided into the cell gap of the cell manipulation panel, where the fluid medium includes wanted cells and unwanted cells, and the unwanted cells are lightened. Then, at procedure 930, the controller of the cell isolation device may be used to control the cell manipulation panel to capture the cells in the pixels. Subsequently, at procedure 940, the image device is used to obtain the image of the pixels having the cells being captured in the vias. Once the image is obtained, at procedure 950, the controller analyzes the image and determines the pixels having the wanted cells being captured therein and the pixels having the unwanted cells being captured therein. In response to determining the pixels having at least one unwanted cell being captured therein, at procedure 960, the controller controls the cell manipulation panel to release the unwanted cells to the fluid medium. Finally, in response to releasing the unwanted cells, at procedure 970, the fluid medium (with the released unwanted cells) is pumped out from the cell gap. In certain embodiments, an additional procedure may be performed by adding a reagent (such as a specific enzyme) in the fluid medium to lighten the unwanted cells. In one embodiment, the fluid medium being pumped out of the cell gap may be collected, such that the fluid medium being pumped out includes the unwanted cells being filtered.

In certain embodiments, after the method as shown in FIG. 9 is performed to isolate or filter the wanted cells from the unwanted cells, additional procedures may be performed to analyze or process the wanted cells and/or the fluid medium (with the released unwanted cells) being pumped out. For example, Fluidigm Corporation [1] provides a real-time polymerase chain reaction (PCR) analysis for viral detection, in which two chips are provided to respectively perform cell isolation and further PCR analysis. Thus, the cell isolation device according to certain embodiments of the present disclosure may be utilized to replace the chip for cell isolation in the Fluidigm analysis. Details of these additional analysis procedures are not part of the present disclosure, and are thus not elaborated herein.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

REFERENCE

[1] Fluidigm Products & Application, in https://www.fluidigm.com/applications/single-cell-analysis.

What is claimed is:
1. A cell isolation device, comprising:
a cell manipulation panel, comprising:
    a first substrate and a second substrate spaced apart, forming a cell gap therebetween, wherein the cell gap is configured to be provided with a fluid medium having a plurality of cells therein, and the cells comprise wanted cells and unwanted cells;
    an insulating layer disposed on the first substrate, forming a plurality of vias penetrating therethrough;
    a pixel array disposed between the insulating layer and the first substrate, defining a plurality of pixels, wherein each of the pixels has a first thin film transistor (TFT) and corresponds to a corresponding via of the vias, the first TFT comprises a first gate electrode, a first electrode and a second electrode, the first gate electrode is provided with a first gate signal, the first gate signal is switched between an ON signal and an OFF signal, the first TFT is configured to be turned on by providing the ON signal as the first gate signal and to be turned off by providing the OFF signal as the first gate signal, the first electrode is configured to be grounded, and the second electrode is located corresponding to the corresponding via such that the second electrode is partially exposed to the fluid medium in the cell gap through the corresponding via;
    a common electrode disposed on the second substrate, being provided with a common voltage $V_{COM}$; and
    a plurality of bottom electrodes disposed between the insulating layer and the first substrate, wherein each of the bottom electrodes is configured to be provided with a bottom voltage in an operational mode;

an imaging device, disposed on a side of the cell manipulation panel adjacent to one of the first substrate and the second substrate, configured to capture an image of the pixels having cells being captured in the vias; and a controller, communicatively connected to the imaging device and the cell manipulation panel, wherein the controller is configured to:

control a first gate driver to provide either the ON signal or the OFF signal as the first gate signal to each of the pixels;

control a second gate driver to provide a second gate signal to control the first electrode of each of the pixels to be grounded or not to be grounded;

control the cell manipulation panel to capture the cells in the pixels by controlling the first gate driver to provide the OFF signal as the first gate signal to all of the pixels and controlling the second gate driver to provide the second gate signal to control the first electrode of each of the pixels not to be grounded, wherein each of the pixels captures a corresponding one of the cells in the corresponding via from the fluid medium by a dielectrophoresis (DEP) force;

receive the image obtained by the imaging device;

analyze the image and determine the pixels having the wanted cells being captured therein and the pixels having the unwanted cells being captured therein; and in response to determining the pixels having the unwanted cells being captured therein, control the cell manipulation panel to release the unwanted cells to the fluid medium by:

controlling the first gate driver to provide the ON signal as the first gate signal to each of the pixels having the unwanted cells being captured therein, such that in each of the pixels having the unwanted cells being captured therein, the first TFT is turned on, and the first electrode and the second electrode are electrically connected by the first TFT being turned on; and controlling the second gate driver to provide the second gate signal to control the first electrode and the second electrode of each of the pixels having the unwanted cells being captured therein to be grounded.

2. The cell isolation device of claim 1, wherein the cell manipulation panel further comprises:

a plurality of first gate lines, correspondingly connected to the first gate driver and the first gate electrodes of the pixels, wherein each of the first gate lines is configured to provide the first gate signal to the first gate electrode of a corresponding one of the pixels;

a plurality of grounding lines, correspondingly connected to the first electrodes of the pixels;

a plurality of second TFTs, one-to-one correspondingly connected to the grounding lines, wherein each of the second TFTs comprises a second gate electrode, a third electrode and a fourth electrode, the second gate electrode is provided with a second gate signal, the second gate signal is switched between an ON signal and an OFF signal, the third electrode is grounded, and the fourth electrode is electrically connected to a corresponding one of the grounding lines; and a plurality of second gate lines, correspondingly connected to a second gate driver and the second gate electrodes of the second TFTs, wherein each of the second gate lines is configured to provide a second gate signal to the second gate electrodes of the of a corresponding one of the second TFTs.

3. The cell isolation device of claim 2, wherein the controller is configured to the cell manipulation panel to capture the cells in the pixels by:

controlling the first gate driver to provide the OFF signal as the first gate signals to all of the pixels through the first gate lines; and controlling the second gate driver to provide the OFF signal as the second gate signals to the second gate electrodes of all of the second TFTs through the second gate lines.

4. The cell isolation device of claim 2, wherein the controller is configured to control the cell manipulation panel to release the unwanted cells to the fluid medium by:

determining a specific pixel of the pixels to have one of the unwanted cells being captured therein;

controlling the first gate driver to provide the ON signal as the first gate signal to the specific pixel through a corresponding one of the first gate lines; and controlling the second gate driver to provide the ON signal as the second gate signal to the second gate electrode of a corresponding one of the second TFTs through the second gate lines, such that the corresponding one of the second TFTs is turned on, and the first electrode of the specific pixel is grounded through a corresponding one of the grounding lines being connected to the corresponding one of the second TFTs.

5. The cell isolation device of claim 2, wherein the controller is configured to control the cell manipulation panel to release the unwanted cells to the fluid medium by:

determining a specific pixel of the pixels to have one of the unwanted cells being captured therein;

controlling the second gate driver to sequentially provide the ON signal as the second gate signal to the second gate electrode of each of the second TFTs through the second gate lines; and when a corresponding one of the second TFTs is turned on, such that the first electrode of the specific pixel is grounded through a corresponding one of the grounding lines being connected to the corresponding one of the second TFTs, controlling the first gate driver to provide the ON signal as the first gate signal to the specific pixel through a corresponding one of the first gate lines.

6. The cell isolation device of claim 1, wherein the bottom voltage is an inverse signal of the common voltage to increase the DEP force.

7. The cell isolation device of claim 1, wherein each of the vias has a diameter of 5 um, a pitch between two adjacent ones of the vias is in a range of 20-50 um, and each of the cells has a cell diameter of 5 um.

* * * * *